US009527915B2

(12) United States Patent
Buchsbaum et al.

(10) Patent No.: US 9,527,915 B2
(45) Date of Patent: Dec. 27, 2016

(54) TREATING BASAL-LIKE GENOTYPE CANCERS

(75) Inventors: Donald J. Buchsbaum, Alabaster, AL (US); Tong Zhou, Birmingham, AL (US); Albert F. LoBuglio, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 1355 days.

(21) Appl. No.: 12/940,746

(22) Filed: Nov. 5, 2010

(65) Prior Publication Data

US 2011/0104143 A1 May 5, 2011

Related U.S. Application Data

(60) Provisional application No. 61/258,274, filed on Nov. 5, 2009.

(51) Int. Cl.
*A61K 39/395* (2006.01)
*G01N 33/50* (2006.01)
*C07K 16/28* (2006.01)

(52) U.S. Cl.
CPC ....... *C07K 16/2878* (2013.01); *C07K 2317/34* (2013.01); *C07K 2317/73* (2013.01)

(58) Field of Classification Search
CPC .... G01N 33/53; G01N 33/50; G01N 33/5044; G01N 33/5091; G01N 33/574; A61K 39/395; A61K 39/39533; A61K 39/39558; C07K 16/28; C07K 16/2875
See application file for complete search history.

(56) References Cited

U.S. PATENT DOCUMENTS

| | | | |
|---|---|---|---|
| 6,313,269 B1 | 11/2001 | Deen et al. | |
| 6,417,328 B2 | 7/2002 | Alnemri | |
| 6,756,196 B2 | 6/2004 | Bertin | |
| 8,278,293 B2 * | 10/2012 | Wang et al. | 514/183 |
| 8,703,712 B2 * | 4/2014 | Buchsbaum et al. | 514/18.9 |
| 2008/0248046 A1 | 10/2008 | Ni et al. | |

FOREIGN PATENT DOCUMENTS

| | | |
|---|---|---|
| CN | 1750843 | 3/2006 |
| WO | WO9832856 | 7/1998 |
| WO | WO9835986 | 8/1998 |
| WO | WO9841629 | 9/1998 |
| WO | WO9846642 | 10/1998 |
| WO | WO9902653 | 1/1999 |
| WO | WO9903992 | 1/1999 |
| WO | WO9909165 | 2/1999 |
| WO | WO9911791 | 3/1999 |
| WO | WO9912963 | 3/1999 |
| WO | WO0066156 | 11/2000 |
| WO | WO0183560 | 11/2001 |
| WO | WO03037913 | 5/2003 |
| WO | 2004050895 | 6/2004 |
| WO | WO2006083937 | 8/2006 |
| WO | 2008/128171 | 10/2008 |

OTHER PUBLICATIONS

Londono-Joshi, A. I., et al., Breast Cancer Res. Treat. 133: 437-445, 2012.*
Ashhab et al., "Two splicing variants of a new inhibitor of apoptosis gene with different biological properties and tissue distribution pattern," FEBS Lett. 495:56-60 (2001).
Badve and Nakshatri, "Oestrogen-receptor-positive breast cancer: towards bridging histopathological and molecular classifications," J. Clin. Pathol. 62:6-12 (2009).
Bodmer et al., "TRAIL receptor-2 signals apoptosis through FADD and caspase," Nat. Cell Biol. 2:241-3 (2000).
Buchsbaum et al., "Antitumor efficacy of TRA-8 anti-DR5 monoclonal antibody alone or in combination with chemotherapy and/or radiation therapy in a human breast cancer model," Clin. Cancer Res. 9:3731-41 (2003).
Buchsbaum et al., "TRAIL receptor-targeted therapy," Future Oncol. 2:493-508 (2006).
Carey et al., "The triple-neagative paradox: primary tumor chemosensitivity of breast cancer subtypes," Clin. Cancer Res. 13:2329-34 (2007).
Chaudhary et al., "Death receptor 5, a new member of the TNFR family, and DR4 induce FADD-dependent apoptosis and activate the NF-kB pathway," Immunity 7:821-30 (1997).
Cheang et al., "Basal-like breast cancer defined by five biomarkers has superior prognostic value than triple-negative phenotype," Clin. Cancer Res. 14:1368-76 (2008).
Conforti et al., "Discrepancy between triple-negative phenotype and basallike tumor: an immunohistochemical analysis based on 150 'triple-negative' breast cancers," Breast Cancer Res. Treat. 106:S135 (2007).
Crook et al., "An apoptosis-inhibiting baculovirus gene with a zinc finger-like motif," J. Virol. 67:2168-74 (1993).
Delmas et al., "Resveratrol-induced apoptosis is associated with Fas redistribution in the rafts and the formation of a death-inducing signaling complex in colon cancer cells," J. Biol. Chem. 278:41482-90 (2003).
DeRosier et al., "TRA-8 anti-DR5 monoclonal antibody and gemcitabine induce apoptosis and inhibit radiologically validated orthotopic pancreatic tumor growth," Mol. Cancer Ther. 6:3198-207 (2007).
DeRosier et al., "Combination treatment with TRA-8 anti-death receptor-5 antibody and CPT-11 induces tumor regression in an orthotopic model of pancreatic cancer," Clin. Cancer Res. 13:5535-43 (2007).

(Continued)

*Primary Examiner* — Misook Yu
*Assistant Examiner* — Anne Holleran
(74) *Attorney, Agent, or Firm* — Kilpatrick Townsend & Stockton LLP

(57) ABSTRACT

Provided herein are methods of treating a subject with cancer comprising administering to the subject a death receptor agonist. Also provided herein are methods of screening a breast cancer cell for responsiveness to a DR5 agonist. Further provided herein are antibodies that selectively bind an N-terminal CARD of DDX3, a DDX3 lacking an N-terminal CARD, and an 80 kDa baculovirus TAP repeat (BIR).

13 Claims, 17 Drawing Sheets

(56) References Cited

OTHER PUBLICATIONS

Desagher and Martinou, "Mitochondria as the central control point of apoptosis," Trends Cell Biol. 10:369-77 (2000).
Deveraux et al., "X-linked IAP is a direct inhibitor of cell-death proteases," Nature 388:300-4 (1997).
Deveraux and Reed, "IAP family proteins-suppressors of apoptosis," Genes Dev. 13:239-52 (1999).
Estes et al., "Efficacy of anti-death receptor 5 (DR5) antibody (TRA-8) against primary human ovarian carcinoma using a novel ex vivo tissue slice model," Gynecol. Oncol. 105:291-8 (2007).
Fiveash et al., "Enhancement of glioma radiation therapy and chemotherapy response with targeted antibody therapy against death receptor 5," Int. J. Radiat. Oncol. Biol. Phys. 71:507-16 (2008).
Honeth et al., "The CD44+/CD24− phenotype is enriched in basal-like tumors," Breast Cancer Res. 10:R53 (2008).
Ichikawa et al., "Tumoricidal activity of a novel anti-human DR5 monoclonal antibody without hepatocyte cytotoxicity," Nat. Med. 7:954-60 (2001).
Ichikawa et al., "TRAIL-R2 (DR5) mediates apoptosis of synovial fibroblasts in rheumatoid arthritis," J. Immunol. 171:1061-9 (2003).
Isakoff et al., "p63/p73 expression mediates cisplatin sensitivity in a subset of triple-negative primary breast cancer: Implications for a new clinical trial," J. Clin. Oncol. 25:10522 (Abstract) (2007).
Johnston et al., "Role of the TRAIL/APO2-L death receptors in chlorambucil- and fludarabine-induced apoptosis in chronic lymphocytic leukemia," Oncogene 22:8356-69 (2003).
Kaliberov et al., "Enhanced apoptosis following treatment with TRA-8 anti-human DR5 monoclonal antibody and overexpression of exogenous Bax in human glioma cells," Gene Ther. 11:658-67 (2004).
Kang et al., "Mda-5: an interferon-inducible putative RNA helicase with double-stranded RNA-dependent ATPase activity and melanoma growth-suppressive properties," Proc. Natl. Acad. Sci. USA 99:637-42 (2002).
Kasof and Gomes, "Livin, a novel inhibitor of apoptosis protein family member," J. Biol. Chem. 276:3238-46 (2001).
Kendrick et al., "Anti-tumor activity of the TRA-8 anti-DR5 antibody in combination with cisplatin in an ex vivo human cervical cancer model," Gyencol. Oncol. 108:591-7 (2008).
Kim et al., "Early therapy evaluation of combined anti-death receptor 5 antibody and gemcitibane in orthotopic pancreatic tumor xenografts by diffusion-weighted magnetic resonance imaging," Cancer Res. 68:8369-76 (2008).
Krammer, "CD95's deadly mission in the immune system," Nature 407:789-95 (2000).
Kristensen et al., "Gene expression profiling of breast cancer in relation to estrogen receptor status and estrogen-metabolizing enzymes: clinical implications," Clin. Cancer Res. 11:878-83 (2005).
Kuang et al., "FADD is required for DR4- and DR5-medaited apoptosis: Lack of TRAIL-induced apoptosis in FADD-deficient mouse embryonic fibroblasts," J. Biol. Chem. 275:25065-8 (2000).
Lam et al., "Comparison of DR5 and Fas expression levels relative to the chemosensitivity of acute lymphoblastic leukemia cell lines," Leuk. Res. 26:503-13 (2002).
Li et al., "Inducible resistance of tumor cells to tumor necrosis factor-related apoptosis-inducing ligand receptor 2-mediated apoptosis by generation of a blockade at the death domain function," Cancer Res. 66:8520-8 (2006).
Li et al., "Intrinsic resistance of tumorigenic breast cancer cells to chemotherapy," J. Natl. Cancer Inst. 100:672-9 (2008).
Liedtke et al., "Differential response to primary chemotherapy and long-term survival in patients with triple-negative breast cancer," J. Clin. Oncol. 25:10519 (2007).
Long et al., "TRA-8 (TRAIL-R2 antibody) based combination chemotherapy produces a survival benefit in a pancreatic cancer orthotopic model," J. Surg. Res. 137:167 (2007).

Magnifico et al., "Tumor-intiating cells of HER2-positive carcinoma cell lines express the highest oncopotein levels and are sensitive to trastuzumab," Clin. Cancer Res. 15:2010-21 (2009).
Mano et al., "The 17q12-q21 amplicon: Her2 and topoisomerase and their importance to the biology of solid tumors," Cancer Treat Rev. 33:64-77 (2007).
Naka et al., "Effects of tumor necrosis factor-related apoptosis-inducing ligand alone and in combination with chemotherapeutic agents on patients' colon tumors grown in SCID mice," Cancer Res. 62:5800-6 (2002).
Ohtsuka and Zhou, "Bisindolymaleimide VII enhances DR5-mediated apoptosis through the MKK4/JNK/p38 kinase and the mitochondrial pathways," J. Biol. Chem. 277:29294-303 (2002).
Ohtsuka et al., "Synergistic induction of tumor cell apoptosis by death receptor antibody and chemotherapy agent through JNK/p38 and mitochondrial death pathway," Oncogene 22:2034-44 (2003).
Oliver et al., "Treatment of human colon cancer xenografts with TRA-8 anti-death receptor 5 antibody alone or in combination with CPT-11," Clin. Cancer Res. 14:2180-9 (2008).
Pan et al., "Caspase-9, Bcl-XL, and Apaf-1 form a ternary complex," J. Biol. Chem. 273:5841-5 (1998).
Rahman et al., "TRAIL induces apoptosis in triple-negative breast cancer cells with a mesenchymal phenotype," Breast Cancer Res. Treat. 113:217-30 (2009).
Rajeshkumar et al., "Tigatuzumab (CS-1008), a novel humanized DR5 agonist antibody, eradicates pancreas cancer stem cells and results in long term cures, in combination with gemcitabine, in direct pancreas cancer xenografts," Amer. Assoc. Cancer Res. Annual Meeting; Denver, CO (2009).
Rakha et al., "Basal-like breast cancer: a critical review," J. Clin. Oncol. 26:2568-81 (2008).
Saleh et al., "A phase I study of CS-1008 (humanized monoclonal antibody targeting death receptor 5 or DR5), administered weekly to patients with advanced solid tumors or lymphomas," J. Clin. Oncol. 26:3537 (2008).
Satyamoorthy et al., "No longer a molecular black-box-new clues to apoptosis and drug resistance in melanoma," Trends Mol. Med. 7:191-4 (2001).
Scaffidi et al., "Two CD95 (Apo-1/Fas) signaling pathways," EMBO J. 17:1675-87 (1998).
Schneider et al., "TRAIL recptors 1 (DR4) and 2 (DR5) signal FADD-dependent apoptosis and activate NF-kB," Immunity 7:831-6 (1997).
Rahman et al., "The TRAIL to target therapy of breast cancer," Adv. Cancer Res. 103:43-73 (2009).
Singh et al., "Synergistic interactions of chemotherapeutic drugs and tumor necrosis factor-related apoptosis-inducing ligand/Apo-2 ligand on apoptosis and on regression of breast carcinoma in vivo," Cancer Res. 63:5390-400 (2003).
Sprick et al., "FADD/MORT1 and caspase-8 are recruited to TRAIL receptors 1 and 2 and are essential for apoptosis mediated by TRAIL receptor 2," Immunity 12:599-609 (2000).
Straughn et al., "Anti-tumor activity of TRA-8 anti-death receptor (DR5) monoclonal antibody in combination with chemotherapy and radiation therapy in a cervical cancer model," Gynecol. Oncol. 101:46-54 (2006).
Suzuki et al., "X-linked inhibitor of apoptosis protein (XIAP) inhibits caspase-3 and -7 in distinct modes," J. Biol. Chem. 276:27058-63 (2001).
Thomas et al., "TNF-related apoptosis-inducing ligand (TRAIL) induces apoptosis in fas-ligand resistant melanoma cells and mediates CD4 T cell killing of target cells," J. Immunol. 161:2195-20 (1998).
Vogler et al., "Targeting XIAP bypasses Bcl-2-mediated resistance to TRAIL and cooperates with TRAIL to suppress pancreatic cancer growth in vitro and in vivo," Cancer Res. 68:7956-65 (2008).
Vucic et al., "ML-IAP, a novel inhibitor of apoptosis that is preferentially expressed in human melanomas," Curr. Biol. 10:1359-66 (2000).
Vucic and Fairbrother, "The inhibitor of apoptosis proteins as therapeutic targetsin cancer," Clin. Cancer Res. 13:5995-6000 (2007).

(56) References Cited

OTHER PUBLICATIONS

Walczak et al., "TRAIL-R2: A novel apoptosis-medaiting receptor for TRAIL," EMBO J. 16:5386-97 (1997).
Wen et al., "Antileukemic drugs increase death receptor 5 levels and enhance Apo-2L-induced apoptosis of human leukemia cells," Blood 96:3900-6 (2000).
Wieland et al., "Molecular characterization of the DICE1 (DDX26) tumor suprressor gene in lung carcinoma cells," Oncol. Res. 12:491-500 (2001).
Wu et al., "Enhancement of TRAIL/Apo2L-mediated apoptosis byadriamycin through inducing DR4 and DR5 in renal cell carcinoma cells," Int. J. Cancer 104:409-17 (2003).
Zhou et al., "Immunobiology of tumor necrosis factor receptor superfamily," Immunol. Res. 26:323-36 (2002).
Zhou et al., "DDX3 associates with DR5 and negatively regulates apoptosis signal transduction of the death domain," NCI Translation Science Meeting: Abstract (Nov. 7, 2008).
Zhou et al., "Anti-DR5 antibody therapy for triple negative breast cancer," NCI Translational Science Meeting: Abstract (Nov. 5-7, 2009).
Burgess, "Behind the scenes of a breakthrough," Crossroads: Cancer Center Magazine (Spring 2009).
"Cancer: Monoclonal Antibody, Anybody," UAB Magazine: http://www.uab.edu/uabmagazine/breakthroughs/research/cancer (Sep. 2008).
"UAB wins $6.4 million nonprofit grant to fight aggressive breast cancer," UAB Media Relations: http://main.uab.edu/Sites/MediaRelations/articles/61698 (Apr. 10, 2009).

Patsy G. Oliver et al., "Effect of anti-DR5 and chemotherapy on basal-like breast cancer", Breast Cancer Res. Treat. Jun. 2012 ; 133(2): 417-426.
Communication pursuant to Article 94(3) EPC for European Patent Application No. 10779874.6 mailed Jul. 15, 2014.
Bockbrader et al., "A small molecule Smac-mimic compound induces apoptosis and sensitizes TRAIL- and etoposide-induced apoptosis in breast cancer cells", Oncogene, 2005, vol. 24, No. 49, pp. 7381-7388.
Foster et al., "Targeting inhibitor of apoptosis proteins in combination with ErbB antagonists in breast cancer", Breast Cancer Research, 2009, vol. 11, No. 3, pp. 1-13.
Keane et al., "Chemotherapy Augments TRAIL-induced Apoptosis in Breast Cell Lines", Cancer Research, 1999, vol. 59, No. 3, pp. 734-741.
Office Action for Chinese Patent Application No. 201080050206.5 mailed Oct. 22, 2014 along with an English translation.
Office Action for Japanese Patent Application No. 2012-538038 mailed Nov. 6, 2014 along with an English translation.
Varfolomeev et al., "X Chromosome-linked Inhibitor of Apoptosis Regulates Cell Death Induction by Proapoptotic Receptor Agonists", Journal of Biological Chemistry, 2009, vol. 284, No. 50, pp. 34553-34560.
Zinonos et al., "Apomab, a fully human agonistic antibody to DR5, exhibits potent antitumor activity against primary and metastatic breast cancer", Mol Cancer Ther 2009, vol. 8, No. 10, pp. 2969-2980.

* cited by examiner

PRELARAGFYYIGPGDRVACFACGGKLSNWEPKDLAMSEHRRHFPNCPF
PTDLARAGFYYIGPGDRVACFACGGKLSNWEPKDLAMSEHLRHFPKCPF
PRELASAGLYYTGTGDQVQCFQCGGKLKNWEPQDRAWSEHRRHFPNCEF

TREATING BASAL-LIKE GENOTYPE CANCERS

CROSS REFERENCE TO RELATED APPLICATION

This application claims the benefit of U.S. Provisional Application No. 61/258,274, filed on Nov. 5, 2009, which is incorporated by reference herein in its entirety.

BACKGROUND

Triple negative breast cancer (TNBC) represents a significant proportion (about 20-25%) of breast cancer patients. TNBC is characterized by the absence of HER2, estrogen receptor (ER), and progesterone receptor (PR). TNBC has a poor prognosis, and no targeted approach to a therapy has been found to date.

SUMMARY

Provided are methods of treating a subject with cancer. The methods comprise selecting a subject with a breast cancer, wherein the breast cancer is a basal-like genotype cancer and wherein the breast cancer is HER2 non-amplified, and administering to the subject a death receptor agonist.

Optionally, the methods comprise selecting a subject with a breast cancer, wherein the breast cancer has one or more characteristics selected from the group consisting of a luminal cell, HER2 amplified, or basal-like genotype; administering to the subject an IAP inhibitor; and administering to the subject a death receptor agonist.

Also provided are methods of screening a breast cancer cell for responsiveness to a DR5 agonist. The methods comprise detecting a basal-like phenotype in the cancer cell; detecting the cancer cell is HER2 non-amplified; and detecting a reduced level of a DR5/DDX3/cIAP1 complex in the cancer cell as compared to a control.

Also provided are methods of screening a triple negative breast cancer cell for responsiveness to a DR5 agonist. Optionally, the methods comprise detecting a level of a DR5/DDX3/cIAP1 complex in the cell and comparing it to a control. A lower level of complex in the cell as compared to the control indicates responsiveness.

Optionally, the methods comprise detecting in the breast cancer cell a DDX3 lacking an N-terminal caspase-associated recruitment domain (CARD). The DDX3 lacking the N-terminal CARD indicates the breast cancer cell is responsive to a DR5 agonist.

Optionally, the methods comprise detecting in the breast cancer cell IAP proteins including an 80 kDa baculovirus IAP repeat. The 80 kDa baculovirus IAP repeat indicates the breast cancer cell is not responsive to a DR5 agonist.

Further provided are antibodies that selectively bind an N-terminal CARD of DDX3. Also provided are antibodies that selectively bind a DDX3 lacking an N-terminal CARD. Also provided are antibodies that selectively bind IAP proteins including an 80 kDa baculovarius IAP repeat (BIR).

DESCRIPTION OF DRAWINGS

FIG. 2A shows graphs demonstrating increased apoptosis in triple negative basal B SUM159 breast cancer cells treated with a combination of TRA-8 antibody and chemotherapeutic agents (cisplatin, carboplatin, and adriamycin). FIG. 2B shows graphs demonstrating increased apoptosis in triple negative epithelial basal A HCC1937 breast cancer cells treated with a combination of TRA-8 antibody and chemotherapeutic agents (cisplatin, carboplatin, and adriamycin). SUM159 and HCC1937 breast cancer cells were pretreated with the chemotherapeutic agents for 24 hours and then treated with TRA-8 antibody for an additional 24 hours. The cells were treated with TRA-8 antibody alone, chemotherapeutic compounds alone, or with a combination of TRA-8 plus chemotherapeutic compounds. Cell viability was assessed by measurement of ATP levels. Values are represented as a mean and standard deviation (n=4 replicates).

FIG. 4 shows that siRNA-mediated knockdown of DDX3 reverses resistance to DR5-mediated apoptosis.

FIG. 5 shows that DR5-associated DDX3 recruits cIAP1 and inhibits apoptosis via the DDX3 CARD.

FIG. 6 shows that the DR5/DDX3/cIAP1 complex can be quantified in TRA-8 sensitive and resistant cells.

FIG. 7 shows the differences in the DR5/DDX3/cIAP1 complex in triple negative and non-triple negative breast cancer cell lines.

FIG. 8 shows the characteristics of a novel antibody (3H4) recognizing a baculovirus IAP repeat (BIR).

FIG. 9 shows the down modulation of IAPs in the DDX3/IAP complex.

DETAILED DESCRIPTION

Figure 1:
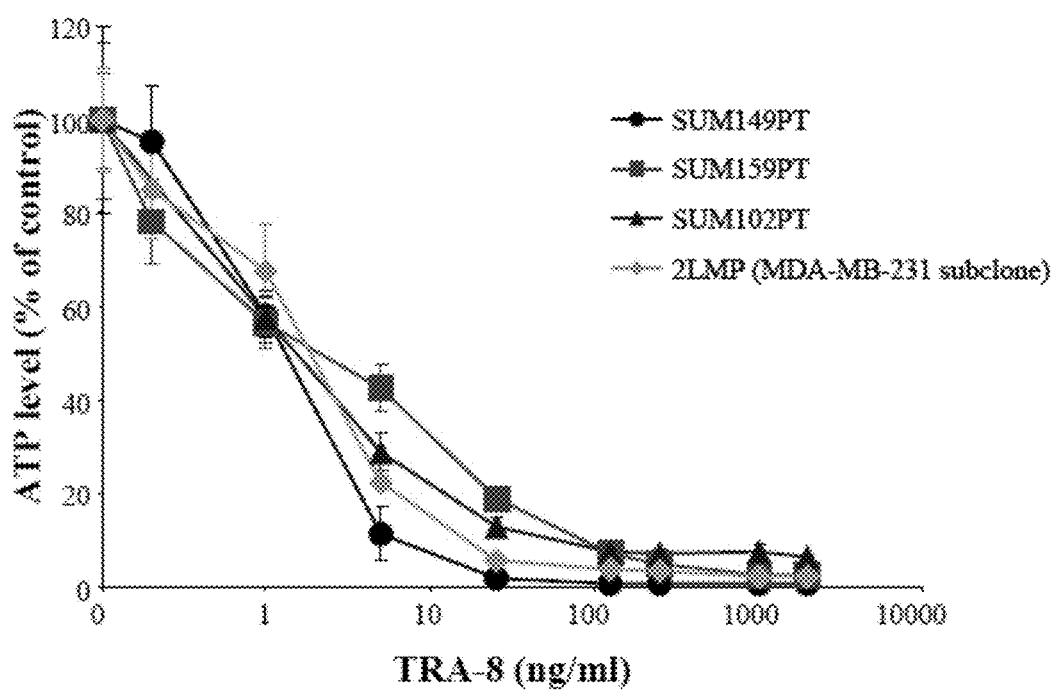
FIG. 1 shows a graph demonstrating that triple negative breast cancer cell lines undergo apoptosis upon treatment with TRA-8. Triple negative breast cancer cell lines were treated with TRA-8 for 24 hours in vitro. Cell viability was assessed using a luciferase based assay to measure ATP levels. Values are represented as a mean and standard deviation (n=6 replicates) relative to untreated control cells.

Provided herein are methods of treating a subject with cancer. The methods comprise selecting a subject with a breast cancer, wherein the breast cancer is a basal-like genotype cancer and wherein the breast cancer is HER2 amplified; and administering to the subject a death receptor agonist. Optionally, a death receptor agonist is a DR5 agonist. Optionally, the DR5 agonist is an antibody. Optionally, the death receptor agonist is administered at three week, two week, or one week intervals.

The methods can, for example, comprise selecting a subject with a breast cancer, wherein the breast cancer has one or more characteristics selected from the group consisting of a luminal cell, HER2 amplified, or basal-like genotype; administering to the subject an IAP inhibitor; and administering to the subject a death receptor agonist. Optionally, the IAP inhibitor is AT-406.

Optionally, the methods further comprise administering to the subject a chemotherapeutic agent. Optionally, the chemotherapeutic agent is administered intravenously every three weeks. Optionally, the chemotherapeutic is selected from the group consisting of adriamycin, paclitaxel, abraxane, cisplatin, and carboplatin.

The breast cancer can, for example, be estrogen receptor negative (ER negative), progesterone receptor negative (PR negative), or both ER negative and PR negative. Optionally, the breast cancer shows reduced levels of a DR5/DDX3/cIAP1 complex as compared to a control. Optionally, the breast cancer comprises a DDX3 lacking a functional N-terminal CARD. For example, the DDX3 lacking a functional N-terminal CARD has a truncated or deleted N-terminal CARD. Alternatively, the DDX3 lacking a functional CARD has a mutation in the N-terminal CARD.

Optionally, the breast cancer is resistant to a chemotherapeutic in the absence of the death receptor agonist. The breast cancer can, for example, be resistant to adriamycin. Optionally, the breast cancer is resistant to paclitaxel. Optionally, the breast cancer is resistant to cisplatin or carboplatin.

The induction of death receptor-mediated apoptosis of tumor cells is a promising approach for cancer therapy. As in most, if not all, therapies, some target cells are resistant. As an example, TRA-8 is a unique agonistic monoclonal anti-DR5 antibody that induces apoptosis of human cancer cells without hepatocyte cytotoxicity (Ichikawa et al., Nat. Med. 7:954-960 (2001)), exhibits strong anti-cancer efficacy in animal models (Buchsbaum et al., Clin. Cancer Res. 9:3731-3741 (2003)) and has demonstrated safety in toxicity studies in non-human primates. Thus, TRA-8 is used as an example herein but other agents that induce apoptosis through death receptor (e.g., DR4 or DR5) activation can be used in the methods taught herein. While TRA-8 and its humanized and human versions are under clinical development as an anti-cancer therapy, some tumor cell lines are resistant to TRA-8-mediated apoptosis despite reasonable levels of DR5 expression. These observations suggest that the resistance is not related to receptor expression but rather to DR5-initiated signaling mechanisms. Certainly DR5-mediated apoptosis can be enhanced significantly by common chemotherapeutic agents (Ohtsuka and Zhou, J. Biol. Chem. 277:29294-29303 (2002); Ohtsuka et al., Oncogene 22:2034-2044 (2003)). While certain cell lines are resistant to TRA-8-mediated apoptosis, other cell lines are susceptible to TRA-8-mediated apoptosis. A class of breast cancers known to have a basal-like phenotype have been identified herein to be susceptible to TRA-8-mediated apoptosis. The basal-like breast cancer cell lines, as demonstrated herein, contain alterations in the DR5/DDX3/cIAP complex that forms in TRA-8 resistant cancer cell lines.

Breast cancers can be divided into at least five distinct molecular subtypes based on gene expression, cellular morphology, and response to treatment. Breast cancers can first be divided into two broad groups, estrogen-receptor (ER)- positive and ER-negative. These two groups can further be subdivided into additional distinct biologically and clinically significant subgroups. ER-positive tumors express estrogen-receptor, ER-responsive genes, and other proteins of luminal epithelial cells. Thus, ER-positive tumors are "luminal tumors," which can further be classified into luminal A and luminal B tumors, depending on the characteristic gene expression patterns.

ER-negative tumors can be further classified into three groups: HER-2 positive, basal-like tumors, and normal breast-like tumors. HER-2 positive tumors express high levels of genes located in the HER2 amplicon on chromosome 17 at location 17q21, including HER-2 and growth factor receptor-bound protein 7 (GRB7). They also have a high level of nuclear factor (NF)-κB activation and express a high level of the transcription factor GATA4 but lack expression of ER and GATA3. The normal breast-like tumors resemble normal breast tissue samples with relatively high expression of many genes characteristic of adipose cells and other nonepithelial cell types, and low levels of expression of luminal epithelial cell genes.

Basal-like tumors express genes characteristic of basal cells. Basal-like gene products have been implicated in cellular proliferation, suppression of apoptosis, cell migration and/or invasion, which are hallmarks of cancer. Basal-like tumors lack expression or express lower levels of ER, ER-responsive genes, and other genes characteristic of luminal epithelial cells. For a complete review of basal-like tumors, see Rakha et al., J. Clin. Oncol. 26:2568-81 (2008).

By "triple negative breast cancer" is meant estrogen-receptor (ER) negative, progesterone-receptor (PR) negative, and HER2 negative breast cancer. Triple negative breast cancers do not express ER, PR, or HER2.

By "HER2 non-amplified" is meant a lack of amplification of the HER2 amplicon located on chromosome 17 at position 17q12-q21. Amplification of the HER2 amplicon can be determined using a fluorescent in situ hybridization (FISH) assay as described in Mano et al., Cancer Treat. Rev. 33:64-77 (2007). Amplification of HER2 is seen in HER2-positive cancers, whereas a lack of amplification of HER2 is seen in basal-like phenotypic breast cancers.

By "death receptor" is meant a receptor that induces cellular apoptosis once bound by a ligand. Death receptors include, for example, tumor necrosis factor (TNF) receptor superfamily members having death domains (e.g., TNFRI, Fas, DR3, 4, 5, 6).

Signal transduction through, for example, DR5 is a key mechanism in the control of DR5-mediated apoptosis. A common feature of the death receptors of the TNFR superfamily is that they all have a conserved "death domain" in their cytoplasmic tail (Zhou et al., Immunol. Res. 26:323-336 (2002)). It is well established that DR5-mediated apoptosis is initiated at the death domain. Crosslinking of DR5 at cell surface by TRAIL or agonistic anti-DR5 antibody leads to oligomerization of DR5, which is immediately followed by the recruitment of FADD to the death domain of DR5 (Bodmer et al., Nat. Cell Biol. 2:241-243 (2000); Chaudhary et al., Immunity 7:821-830 (1997); Kuang et al., J. Biol. Chem. 275:25065-25068 (2000); Schneider et al., Immunity 7:831-836 (1997); Sprick et al., Immunity 12:599-609 (2000)). The death-domain engaged FADD further recruits the initiator procaspase 8 and/or procaspase 10 to form a Death Domain Inducing Signal Complex (DISC) through homophilic DD interactions (Krammer, Nature 407:789-795 (2000)). The activated caspase 8 and 10 may activate caspase 3 directly or may cleave the BH3-containing protein Bid to activate a mitochondria-dependent apoptosis pathway through release of cytochrome C and caspase 9 activation (Desagher and Martinou, Trends Cell Biol. 10:369-377 (2000); Scaffidi et al., EMBO J. 17:1675-1687 (1998)). Following the formation of the death domain complex, several signal transduction pathways are activated such as caspase, NF-κB, and JNK/p38. Activation of these signaling pathways leads to regulation of death receptor-mediated apoptosis through the Bcl-2 and IAP family of proteins.

By "agonist" is meant a substance (molecule, drug, protein, etc.) that is capable of combining with a receptor (e.g., death receptor) on a cell and initiating the same reaction or activity typically produced by the binding of the endogenous ligand (e.g., apoptosis). The agonist of the present method can be a death receptor ligand. Thus, the agonist can be TNF, Fas Ligand, or TRAIL. The agonist can further be a fragment of these ligands comprising the death receptor binding domain such that the fragment is capable of binding and activating the death receptor. The agonist can further be a fusion protein comprising the death receptor binding domain such that the fusion protein is capable of binding and activating the death receptor. The agonist can further be a polypeptide having an amino acid sequence with at least 85% homology to TNF, Fas or TRAIL such that the homologue is capable of binding and activating the death receptor.

The agonist can further be an apoptosis-inducing antibody that binds the death receptor. The "antibody" can be monoclonal, polyclonal, chimeric, single chain, humanized, fully human antibody, or any Fab or F(ab')2 fragments thereof. By "apoptosis-inducing antibody" is meant an antibody that causes programmed cell death either before or after activation using the methods provided herein. Thus, the agonist of the present method can be an antibody specific for a Fas, TNFR1 or TRAIL death receptor, such that the antibody activates the death receptor. The agonist can be an antibody specific for DR4 or DR5. The agonist can be a DR5 antibody having the same epitope specificity, or secreted by, a mouse-mouse hybridoma having ATCC Accession Number PTA-1428 (e.g., the TRA-8 antibody), ATCC Accession Number PTA-1741 (e.g., the TRA-1 antibody), ATCC Accession Number PTA-1742 (e.g., the TRA-10 antibody. The agonist can be an antibody having the same epitope specificity, or secreted by, the hybridoma having ATCC Accession Number PTA-3798 (e.g., the 2E12 antibody).

The TRAIL receptor targeted by the antibody of the present method can be DR4 or DR5. Such receptors are described in published patent applications WO99/03992, WO98/35986, WO98/41629, WO98/32856, WO00/66156, WO98/46642, WO98/5173, WO99/02653, WO99/09165, WO99/11791, WO99/12963 and published U.S. Pat. No. 6,313,269, which are all incorporated herein by reference in their entireties for the receptors taught therein. Monoclonal antibodies specific for these receptors can be generated using methods known in the art. See, e.g., Kohler and Milstein, Nature, 256:495-497 (1975) and Eur. J. Immunol. 6:511-519 (1976), both of which are hereby incorporated by reference in their entirety for these methods. See also methods taught in published patent application WO01/83560, which is incorporated herein by reference in its entirety.

By "CARD" is meant a caspase-associated recruitment domain. Proteins containing a CARD are characterized by the ability to bind a death receptor, wherein binding is optionally outside of the death domain and modulate the activation of apoptosis by the death domain of said death receptor. DDX3 is a representative member of the protein family characterized by containing a CARD.

Proteins containing a CARD have been established as key regulators of cell death. A CARD is composed of a conserved alpha-helical bundle found in the N-terminal of pro-domains of certain caspases. CARDs can also be found in a variety of other proteins. Like the death domain proteins, CARDs function as homotypic protein interaction motifs that allow the communications of proteins via CARD/CARD interactions. The proteins with a CARD can be either pro-apoptotic or anti-apoptotic. The pro-apoptotic CARD domain proteins include certain caspases such as caspase 2, 4, and 9, and Apaf1, which play important roles in the initiation of apoptosis. The representative anti-apoptotic CARD proteins include cIAP1 and cIAP2, which interact with the CARD of caspases, and inhibit caspase activation via their baculovirus IAP repeat (BIR) domain. Many aspects of the function of this family of proteins point to their potential utility as novel drug targets in the treatment of cancer. Several CARD-containing proteins are critical components of the conserved cell death machinery which, when dysregulated, promotes oncogenesis and contributes prominently to tumor resistance to chemotherapy. The pro-apoptotic protein Apaf1, which is inactivated in some cancers, is a CARD protein that is indispensable for mitochondria-induced apoptosis. Other anti-apoptotic CARD proteins, such as the proteins of the IAP family, have been shown to protect tumors from cell death stimuli and to be over-expressed in certain forms of cancer. Therapeutics that activate or inhibit CARD proteins can therefore be utilized as chemo-sensitizing agents or as modulators of apoptosis when used in conjunction with conventional chemotherapy.

The CARD of CARD containing proteins is involved in the recruitment of inhibitors of apoptosis (IAP), which suppress apoptosis in host cells during viral infection (Crook et al., J. Virol. 67:2168-2174 (1993)). The IAP family antagonizes cell death by interacting with and inhibiting the enzymatic activity of mature caspases. Eight distinct mammalian IAPs have been identified, including XIAP, c-IAP1, c-IAP2, and ML-IAP/Livin (see, for example, Ashhab et al., FEBS Lett. 495:56-60 (2001); Kasof and Gomes, J. Biol. Chem. 276:3238-3246 (2001); Vucic et al., Curr. Biol. 10:1359-1366 (2000)). All IAPs contain one to three baculovirus IAP repeat (BIR) domains and have homologous sequence. Through the BIR domain, IAP molecules bind and directly inhibit caspases (Deveraux and Reed, Genes Dev. 13:239-252 (1999); Deveraux et al., Nature 388:300-304 (1997)). The mitochondrial proteins Smac/DIABLO could bind to and antagonize IAPs (Suzuki et al., J. Biol. Chem. 276:27058-27063 (2001)) to suppress IAP function (Wieland et al., Oncol. Res. 12:491-500 (2000))

The DR5/DDX3/cIAP complex can be altered or decreased in level in basal-like phenotypic breast cancer cells. As shown below, the DR5/DDX3/cIAP1 complex can, for example, be altered by containing DDX3 lacking an N-terminal CARD or a DDX3 with a mutation in the N-terminal CARD. The complex containing the DDX3 lacking a functional N-terminal CARD generally dissociates upon treatment with a death receptor agonist, which allows for DR-mediated apoptosis. Lower levels of expression of DDX3 or cIAP may also contribute to lower levels of the DR5/DDX3/cIAP complex within breast cancer cells. Cells with lower levels of the complex are also susceptible to treatment with a death receptor agonist, which allows for DR-mediated apoptosis.

Provided are methods of treating a subject with cancer, comprising administering to the subject a death receptor agonist. The death receptor agonist can, for example, be administered with IAP inhibitors. Optionally, the IAP inhibitor is AT406. The death receptor agonists can also be administered in conjunction with other chemotherapeutic agents. Examples of chemotherapeutic agents include adriamycin, bleomycin, carboplatin, chlorambucil, cisplatin, colchicines, cyclophosphamide, daunorubicin, dactinomycin, diethylstilbestrol, doxorubicin, etoposide, 5-fluorouracil, floxuridine, melphalan, methotrexate, mitomycin, 6-mercaptopurine, paclitaxel, teniposide, 6-thioguanine, vincristine, and vinblastine. Further examples of chemotherapeutic agents are found in The Merck Manual of Diagnosis and Therapy, 18$^{th}$ Ed., Berkow et al., eds, Rahway, N.H. (2005) and Sladek et al., Metabolism and Action of Anti-Cancer Drugs, Powis et al., eds., Taylor and Francis, New York, N.Y. (1987).

Provided herein are methods of treating cancer in a subject. Such methods include administering an effective amount of a death receptor agonist, an IAP inhibitor, a chemotherapeutic agent, or combinations thereof. Optionally, the death receptor agonist, TAP inhibitor, chemotherapeutic agent, and combinations thereof are contained within a pharmaceutical composition.

Provided herein are compositions containing the provided death receptor agonist, TAP inhibitor, chemotherapeutic agent, and combinations thereof, and a pharmaceutically acceptable carrier described herein. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in Remington: The Science and Practice of Pharmacy, 21st Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the death receptor agonist, TAP inhibitor, chemotherapeutic agent, and combinations thereof to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Also provided are methods of screening a breast cancer cell for responsiveness to a DR5 agonist. The methods comprise detecting a basal-like phenotype in the cancer cell; detecting the cancer cell is HER2 non-amplified; and detecting a reduced level of a DR5/DDX3/cIAP1 complex in the cancer cell as compared to a control. The methods can, for example, further comprise determining the cancer cell is estrogen receptor negative (ER negative), progesterone receptor negative (PR negative), or both ER negative and PR negative. Optionally, the DR5 agonist is an antibody. Optionally, the breast cancer cell is derived from a breast biopsy.

Also provided are methods of screening a breast cancer cell (e.g., a triple negative) for responsiveness to a DR5 agonist. The methods can, for example, comprise detecting the level of a DR5/DDX3/cIAP1 complex in the cell and comparing it to a control. A lower level of the complex in the cell as compared to a control indicates the breast cancer cell is responsive to the DR5 agonist. The methods can, for example, comprise detecting in the breast cancer cell a DDX3 lacking a functional N-terminal CARD. The DDX3 lacking a functional N-terminal CARD indicates the breast cancer cell is responsive to a DR5 agonist. The methods can, for example, comprise detecting in the breast cancer cell IAP proteins including an 80 kDa baculovirus IAP repeat (BIR). The 80 kDa BIR indicates the breast cancer cell is not responsive to a DR5 agonist.

Assay techniques that can be used to determine levels of expression of DDX3, DDX3 lacking a functional N-terminal CARD, and IAP proteins including an 80 kDa BIR in a sample are known to those of skill in the art. Such assay methods include a radioimmunoassay (RIA), an immunohistochemistry assay, an in situ hybridization assay, a competitive-binding assay, a Western blot analysis, and an ELISA assay. Assays also include determining a level of RHA using an assay selected from the group consisting of a microarray assay, a gene chip, a Northern blot, an in situ hybridization assay, a reverse-transcription-polymerase chain reaction (RT-PCR) assay, a one step PCR assay, and a real-time quantitative (qRT)-PCR assay. The analytical techniques to determine protein or RNA expression are known. See, e.g., Sambrook et al., Molecular Cloning: A Laboratory Manual, $3^{rd}$ Ed., Cold Spring Harbor Press, Cold Spring Harbor, N.Y. (2001).

Techniques to determine levels of a DR5/DDX3/cIAP complex are also known to those of skill in the art. Assays to determine a level of the complex can be selected from the group consisting of an immunoprecipitation assay, a co-immunoprecipitation assay, and non-gel based approaches, such as mass spectrometry or protein interaction profiling, such as a co-localization assay. The assays are known in the art. See, e.g., Sambrook et al., Molecular Cloning: A Laboratory Manual, 3rd Ed., Cold Spring Harbor Press, Cold Spring Harbor, N.Y. (2001); Dickson, Methods Mol. Biol. 461:735-44 (2008); and Zinchuk et al., Acta Histochem. Cytochem. 40:101-11 (2007).

Also provided are antibodies that selectively bind an N-terminal CARD of DDX3, antibodies that selectively bind a DDX-3 lacking a N-terminal CARD or lacking a functional N-terminal CARD, and antibodies that bind IAP proteins including an 80 kDa baculovirus IAP repeat.

The term antibody is used herein in a broad sense and includes both polyclonal and monoclonal antibodies. The term can also refer to a human antibody and/or a humanized antibody. Examples of techniques for human monoclonal antibody production include those described by Cole et al. (Monoclonal Antibodies and Cancer Therapy, Alan R. Liss, p. 77 (1985)) and by Boerner et al. (J. Immunol. 147(1):86-95 (1991)). Human antibodies (and fragments thereof) can also be produced using phage display libraries (Hoogenboom et al., J. Mol. Biol. 227:381 (1991); Marks et al., J. Mol. Biol. 222:581 (1991)). The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA 90:2551-5 (1993); Jakobovits et al., Nature 362:255-8 (1993); Bruggermann et al., Year in Immunol. 7:33 (1993)).

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g. cancer). The term patient or subject includes human and veterinary subjects.

According to the methods taught herein, the subject is administered an effective amount of the death receptor agonist, IAP inhibitor, chemotherapeutic agent, or any combination thereof. The terms effective amount and effective dosage are used interchangeably. The term effective amount is defined as any amount necessary to produce a desired physiologic response. Effective amounts and schedules for administering the death receptor agonist, IAP inhibitor, chemotherapeutic agent, and combinations thereof may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Optionally, the death receptor agonist is administered at three week, two, week, or one week intervals. Optionally, the chemotherapeutic is administered every three weeks. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

"Optional" or "optionally" means that the subsequently described event, circumstance, or material may or may not occur or be present, and that the description includes instances where the event, circumstance, or material occurs or is present and instances where it does not occur or is not present.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

General Methods
Cell Lines, Antibodies, and Reagents.

Human breast cancer cell line, MDA-MB-231, was purchased from the American Tissue Culture Collection (ATCC) (Manassas, Va.). Human ovarian cancer cell line, UL-3C, was obtained. Cells were maintained in DMEM or RPMI1640 supplemented with 10% heat-inactivated FCS, 50 µg/ml streptomycin, and 50 U/mL penicillin (Cellgro, Mediatech, Inc., Manassas, Va.).

Anti-human DR4 (clone: 2E12) and anti-human DR5 (clone: TRA-8) monoclonal antibodies were previously described (Ichikawa et al., 2003; Ichikawa et al., 2001). Anti-human DR5 (clone: 2B4) was developed for flow cytometry and immunoprecipitation assays. Recombinant soluble TRAIL was purchased from Alexis Biochemicals (San Diego, Calif.). Polyclonal anti-caspase 3 and anti-caspase 8 antibodies were purchased from BD Pharmingen (San Diego, Calif.). Monoclonal anti-human caspase 2, 3, 8, 9 and 10 antibodies, and monoclonal anti-human Bcl-2, Bcl-xL, Bax, cIAP-1, cIAP-2, XIAP, and survivin antibodies, were prepared. Anti-PARP antibody was purchased from Cell Signaling Technology, Inc. (Beverly, Mass.). Anti-β-actin antibody was purchased from Sigma. Anti-FADD were purchased from Transduction Laboratories (Lexington, Ky.). All horseradish peroxidase (HRP)-conjugated secondary reagents were purchased from Southern Biotechnology Associates, Inc. (Birmingham, Ala.).

Active Caspase-1, Caspase-2, Caspase-3, Caspase-6, Caspase-7, Caspase-8, Caspase-9, and Caspase-10 were purchased from EMD Biosciences, Inc (San Diego, Calif.). The fluorogenic peptide derivatives Ac-Val-Asp-Val-Ala-Asp-AMC (Ac-VDVAD-AMC, 260060M001, SEQ ID NO:1), Ac-Asp-Glu-Val-Asp-amino-4-methylcoumarin (Ac-DEVD-AMC, 260031M001, SEQ ID NO:2), and Ac-carbonyl-Ile-Glu-Thr-Asp-7-amido-4-methylcoumarin (Z-IETD-AMC, 260042M001, SEQ ID NO:3) were purchased from Alexis Biochemicals; San Diego, Calif. Caspase-2, -3, -8, -10 inhibitor (FMKSP01) were purchased from R&D Systems, Inc (Minneapolis, Minn.).

Cytotoxicity Analysis of Tumor Cell Susceptibility to TRA-8, 2E12, and TRAIL-Mediated Apoptosis.

Cells (1,000 cells per well) were seeded into 96-well plates in triplicate with eight concentrations (double serial dilutions from 1000 ng/ml) of TRA-8, 2E12, or TRAIL. Cell viability was determined after overnight culture using an ATPLITE™ assay according to the manufacturer's instructions (Packard Instruments, Meriden, Conn.). The results are presented as the precentage of viable cells in treated wells compared to medium control wells.

Flow Cytometry.

Cells ($10^6$) were washed once with PBS and resuspended in 1 ml cold FACS buffer (PBS with 5% FBS and 0.01% $NaN_3$) containing the primary antibody (1 µg/ml of TRA-8). Cells were stained on ice for 60 minutes, then washed with 3 ml cold FACS buffer, and incubated with the secondary antibody (1:100 dilution of PE-conjugated goat anti-mouse IgG) at 4° C. for 60 minutes in the dark. After an additional 3 ml wash with FACS buffer, 10,000 cells per sample were analyzed by FACSCAN flow cytometer (BD Biosciences; San Jose, Calif.).

Western Blot Analysis of Apoptosis-Associated Proteins.

Tumor cells (3×10⁶) were washed twice with cold PBS and lysed with 300 µl lysis buffer containing 10 mM Tris-HCl (pH 7.6), 150 mM NaCl, 0.5 mM EDTA, 1 mM EGTA, 0.1% SDS, 1 mM sodium orthovanadate, and a mixture of protease inhibitors (1 mM phenylmethylsulfonyl fluoride, 1 µg/ml pepstatin A, 2 µg/ml aprotinin). The cell lysates were sonicated for 10 seconds and centrifuged for 20 minutes at 12,000 g. The cell lysates with equal amounts of total proteins were boiled for 5 minutes with SDS-PAGE sample buffer. Total cell lysates were separated in 8%, 10%, or 12% SDS-PAGE, and electrophoretically transferred to a nitrocellulose membrane. The blots were blocked with 5% nonfat dry milk in TBST buffer (20 mM Tris-HCl (pH 7.4), 500 mM NaCl, and 0.1% Tween 20) and incubated with primary antibody in blocking buffer at 4° C. overnight. The blots were washed three times with TBST and probed with HRP-conjugated secondary antibodies for 1 hour at room temperature. After being washed four times with TBST, the probed proteins were visualized using the ECL Western blotting detection system (Amersham Biosciences; Pittsburgh, Pa.) according to the manufacturer's instructions.

siRNA Mediated Knockdown of DDX3.

Design RNAi: an online design tool, BLOCK-iT RNAi Designer (Invitrogen; Carlsbad, Calif.), was used to identify RNAi targets for DDX3. Five targeted siRNA sequences were selected from the top 10 highest scoring RNAi targets (see Table 1).

(Fl=fluorescein); Anti-sense RNA 5'-GUUUC-CCAUGAUAAUUUCUCC-3' (SEQ ID NO:16), and RNAi control oligo (RI-010-DP) was purchased from Molecula (Columbia, Md.).

Generation of Expression Vectors.

The full-length DDX3 was cloned into pcDNA3.1 plasmid (Invitrogen) with a His tag at the N-terminus of DDX3. DDX3 and DR5 cDNA was generated by reverse transcriptase polymerase chain reaction (RT-PCR) performed with total RNA extracted from MDA231 cells using the following primer pair: DDX31 forward primer with BamHI: 5'-acggatccaaatgagtcatgtggcagtgga-3' (SEQ ID NO:17); DDX3662 reverse primer with XhoI: 5'-ctctcgagcaaagcaggctcagttaccc-3' (SEQ ID NO:18). DR5-1 forward primer with KpnI: 5'-aaaggtaccagccatggaacaacggggacag-3' (SEQ ID NO:19); DR5-441 reverse primer with EcoV: 5'-aaagatatcttaggacatggcagagtctgcatt-3' (SEQ ID NO:20); the isolated poly-merase chain reaction fragment of DDX3 was in frame into pcDNA3.1-His vector (Invitrogen). DR5 cDNA was cloned into the pshutter-CMV vector. The correct sequences were confirmed by DNA sequencing.

DDX3/pcDNA3.1-His expression plasmid was generated by deleting the DDX3 sequence between the BamHI and XhoI sites. DDX3151 forward primer with BamHI: 5'-acggatccaaatgttttctggaggcaacactggg-3' (SEQ ID NO:21); DR5/pshutter-CMV expression plasmid was generated by deleting the DR5 sequence using the following primer: DR5-340 reverse primer with EcoRV: 5'-aaagatatcttactgtctcagagtctca-

TABLE 1

| siRNA orientation: SENSE-loop-ANTISENSE | | | |
|---|---|---|---|
| Construct | Strand | Sequence | |
| 1  108-128 | top | CACCAAGCTTGCGCTATATTCCTCCTCATTTcgaaAAA TGAGGAGGAATATAGCGCCTCGAG | SEQ ID NO: 4 |
| | bottom | AAAACTCGAGGCGCTATATTCCTCCTCATTTttcgAAA TGAGGAGGAATATAGCGCAAGCTT | SEQ ID NO: 5 |
| 2  562-582 | top | CACCGGAGAAATTATCATGGGAAACcgaaGTTTCCCA TGATAATTTCTCC | SEQ ID NO: 6 |
| | bottom | AAAAGGAGAAATTATCATGGGAAACttcgGTTTCCCA TGATAATTTCTCC | SEQ ID NO: 7 |
| 3  1554-1574 | top | CACCGCCAAGTGATATTGAAGAATAaacgTATTCTTC AATATCACTTGGC | SEQ ID NO: 8 |
| | bottom | AAAAGCCAAGTGATATTGAAGAATAcgttTATTCTTC AATATCACTTGGC | SEQ ID NO: 9 |
| 4  5'UTR | top | CACCGCTTTCCAGCGGGTATATTAGcgaaCTAATATA CCCGCTGGAAAGC | SEQ ID NO: 10 |
| | bottom | AAAAGCTTTCCAGCGGGTATATTAGttcgCTAATATAC CGCTGGAAAGC | SEQ ID NO: 11 |
| 5  1045-1065 | top | CACCGCTGATCGGATGTTGGATATGcgaaCATATCCA ACATCCGATCAGC | SEQ ID NO: 12 |
| | bottom | AAAAGCTGATCGGATGTTGGATATGttcgCATATCCA ACATCCGATCAGC | SEQ ID NO: 13 |

They were then cloned into the BLOCK-iT U6 entry vector. The siRNA is driven by the U6 promoter and can be transiently expressed in most dividing or nondividing mammalian cell types. Resistant cells were transfected with RNAi used LIPOFECTAMINE 2000 (Invitrogen; Carlsbad, Calif.) for the RNAi response. The decreased DDX3 expression was determined by Western blot analysis using anti-DDX3 antibody 36 hours after transfection. Once decreased DDX3 expression was achieved, the siRNA oligo was synthesized (Target sequence: GGAGAAATTAT-CATGGGAAAC (SEQ ID NO:14): Sense RNA 5'-Fl-GGA-GAAAUUAUCAUGGGAAAC (Fl-SEQ ID NO:15)

gtgggatc-3' (SEQ ID NO:22); DR5-330 reverse primer with EcoRV and XhoI: 5'-aaagatatcctcgagatttgctggaaccagcagcct-3' (SEQ ID NO:23).

Constructions of Expression Plasmids for DDX3 in Bacteria.

DDX3 or cIAP1 fragment was inserted into the TOPO100 vector (Invitrogen). The resulting plasmids were transformed into the E. coli strain BL21 (DE3), which was grown in LB media to exponential phases and induced with 0.4 mM isopropyl-1-thio-β-D-galactopyranoside for 3 hours. Cells were pelleted, resuspended in lysis buffer (30 mM Tris-HCl, pH 7.5, 0.1 mM NaCl, 1 mM DTT, 0.1 mM EDTA, 1%

Nonidet P-40, and 20 μg/ml PMSF), and sonicated. The supernatant after centrifugation at 14,000×g for 15 minutes was purified by Ni column. The protein concentration was determined by BCA assay (Pierce, Rockford, Ill.), and aliquots were stored at 80° C.

Transient Transfections of 293 or 3T3 Cells.

293 or 3T3 cells were transfected with expression vectors using LIPOFECTAMINE™ 2000 (Invitrogen). After 24 hours following transfection, protein expression was determined by Western blot analysis using respective monoclonal antibody. For co-immunoprecipitation analysis, cells were lysed with immunoprecipitation-lysis buffer containing a protease inhibitor cocktail.

Co-Immunoprecipitation Assay.

Anti-DDX3 or anti-DR5 antibody was conjugated to Sepharose beads (Sigma; St. Louis, Mo.). The composition of the DR5 DISC was determined as follows. 5×10$^6$ cells (if not otherwise indicated) were treated with 500 ng/ml of TRA-8 for the indicated time at 37° C. and then lysed in immunoprecipitation lysis buffer (20 mM Tris-HCl, pH 7.4, 150 mM NaCl, 0.2% NONIDET P40, and 10% glycerol and complete protease inhibitor cock-tail) or lysed without treatment (unstimulated condition). The DR5 DISC was then precipitated overnight at 4° C. with 30 μl beads. After immunoprecipitation, the beads were washed four times with lysis buffer. The beads were then washed five times with 10 mM Tris buffer and resuspended in loading buffer for SDS-PAGE and immunoblotting analyses.

Assay of Caspase Activity in vitro.

Fluorometric assays were conducted in 96-well clear bottom plates, and all measurements were carried out in triplicate wells. 100 μl of assay buffer (10 mM HEPES pH 7.0, 50 mM NaCl, 2 mM MgCl$_2$, 5 mM EDTA, and 1 mM DTT) was added. Active caspase-8 and peptide substrates (Ac-IETD-AMC) were added to each well to a final concentration of 100 ng/μl. Co-immunoprecipitation eluted fraction was added to start the reaction. Background fluorescence was measured in wells containing assay buffer, substrate, and lysis buffer without the cell lysates. Assay plates were incubated at 37° C. for 1 hour. Fluorescence was measured on a fluorescence plate reader (Bio-Tek; Winooski, Vt.) set at 355-nm excitation and 440-nm emission.

in vitro Caspase Cleavage Assay.

The ability of caspases to cleave DDX3 was examined in an in vitro assay. The cleavage reactions carried out for 30 minutes at 37° C., including 10 μl of eluted fraction from DR5 co-IP, 10 μl of reaction buffer (10 mM HEPES [pH 7.0], 50 mM NaCl, 2 mM MgCl$_2$, 5 mM EGTA, 1 mM DTT, 2 mM ATP), and 5 ul (0.1 U/μl) recombinant active forms of caspases. The cleavage was determined by Western blot with anti-DDX3 antibody.

Example 1

Role of DDX3 in TRAIL-R2-Mediated Apoptosis

Proteomics analysis of a candidate protein, DDX3, that causes a blockade of the death domain of DR5 in resistant cells. The spontaneously developed or induced apoptosis resistance to the therapeutic agents, TRAIL and agonistic antibodies, that target the death receptors represents a major obstacle in effective treatment of cancer with these agents. In order to determine whether alternative compositions of DR5 death domain complexes are present in resistant cells, the proteomic profiles of existing DR5-associated proteins were compared in TRA-8-sensitive parental and TRA-8-resistant MDA231 cells before and after TRA-8 treatment by two-dimensional proteomic and mass spectrometry analysis. In the examination of two-dimensional gels stained with SYPRO™ ruby (Molecular Probes; Eugene, Oreg.), a protein spot about ~80 kDa was found. The association of this protein with DR5 blocked the formation of DR5 Death Domain Inducing Signal Complex (DISC), thereby causing TRA-8 resistance. The ~80 kDa protein was excised from SDS-PAGE and digested with trypsin, and peptide sequences were analyzed by mass sepectrometry. The protein amino acid sequences from six digested fragments were 100% identical to the Genbank sequence of human DDX3 (Table 2), indicating that DDX3 disassociates from DR5 during TRA-8-induced apoptosis. If this protein remains associated with the DR5-associated protein complex, it can prevent FADD recruitment and cause failure of DISC formation.

TABLE 2

DDX3 Fragments.

| Peptide | Sequence | DDX3 | SEQ ID |
|---|---|---|---|
| 1 | HVINFDLPSDIEEYVHR | aa512-528 | SEQ ID NO: 24 |
| 2 | DFLDEYIFLAVGR | aa395-407 | SEQ ID NO: 25 |
| 3 | DLLDLLVEAK | aa555-564 | SEQ ID NO: 26 |
| 4 | SFLLDLLNATGK | aa429-440 | SEQ ID NO: 27 |
| 5 | TAAFLLPILSQIYSDGPGEALR | aa231-252 | SEQ ID NO: 28 |
| 6 | QYPISLVLAPT | aa265-275 | SEQ ID NO: 29 |

DDX3 is a DR5-associated protein in DR5-mediated apoptosis. To determine whether DDX3 is indeed associated with DR5, the full-length (amino acids 1-662), N-terminal fragment (amino acids 1-316), and a C-terminal fragment (amino acids 310-662) of DDX3 were cloned into PCD-NAIII3.1 with a 6-His tag at the N-terminus These expression vectors were transfected into MDA231 parental cells to achieve overexpression of the recombinant full-length and deletion mutants of DDX3. Only full-length DDX3, not its N-terminal and C-terminal deletion mutants, was associated with DR5 as detected by co-immunoprecipitation analysis followed by Western blot analysis using anti-6-His antibody. These results confirmed that full-length DDX3 associated with DR5. DDX3 was immunoprecipitated with anti-DR5 in MDA231 cells.

To further confirm the association of DDX3 with DR5, N-terminal deletion versions, C-terminal deletion versions, and full-length versions of DDX3 were expressed in E. coli. Proteins were purified and used as an antigen to generate polyclonal and a panel of monoclonal antibodies against DDX3. DR5-associated DDX3 was detected by co-immunoprecipitation and Western blot analysis using mouse anti-DDX3 monoclonal antibody. The results demonstrated that DDX3 was co-immunoprecipitated with DR5 in both non-apoptotic parental and resistant cells. There was a time-dependent decrease of DDX3 in TRA-8-sensitive cells but not in TRA-8-resistant cells during apoptosis. In addition, by Western blot analysis, a rapid decrease and cleavage of DR5-associated DDX3 during TRA-8-induced apoptosis was observed. This indicated that the cleavage of DDX3 is caspase-dependent. Based on these results, the DDX3 sequence was scrutinized for potential cleavage sites at the N-terminal, and a relatively conserved caspase cleavage motif DKSDEDD (SEQ ID NO:30) was found at amino acids 129-135. It is apparent that cleavage occurs on the DISC and results in a critical functional element of DDX3 being released from DR5. The data were compatible with the latter model, which suggests that initiated caspase is rapidly recruited to DR5 and cleaves DDX3 readily. In addition, FADD and caspase-8 associate with and recruit to DR5 to form DISC, which in turn leads to caspase cascade activation correlated to the DR5-associated DDX3 cleavage. This indicates that in certain circumstances DDX3 is essential for the apoptotic program, illustrating that DDX3 associates with DR5 and is involved in DR5-mediated apoptosis resistance.

Mapping interaction region of DDX3 with DR5. In order to better understand the regulation of DDX3 in DR5-mediated signal transduction, the approximate DDX3 region that is required for binding DR5 was determined using HEK293A cells that had been transiently transfected with plasmids encoding deletion mutants of DDX3. The interaction of recombinant DDX3 and DR5 was determined by co-immunoprecipitation using TRA-8, full-length DDX3, DDX3Δ201-662, or DDX3Δ1-400 bound to DR5. However, neither DDX3Δ251-662 nor DDX3Δ1-350 could bind to DR5. This indicates that DDX3 has two binding motifs at DR5. One is located at the N-terminus (amino acids 200-250); the other is adjacent to amino acids 350-400. Western blot analysis of lysates from the same cells confirmed the production of comparable amounts of wild-type DDX3 and deletion fragments of DDX3, which exclude differences in protein expression as an explanation for these results.

DDX3 is permanently associated with DR5 and correlates with the blockade of FADD recruitment in TRA-8-resistant cells, indicating that the DR5-associated DDX3 prevents the recruitment of FADD. There can be a connection between DDX3 and FADD through DR5. To test whether DDX3 and FADD share a common binding motif at the death domain of DR5 or the two binding motifs are close together, so that pre-engaged DDX3 interferes with the recruitment of FADD, the location of the DDX3-binding domain in DR5 was determined Vectors encoding the full-length DR5, and a series of amino-terminal domain deletions of DR5, including complete deletion of death domain, were constructed. In an analogous approach to assess the function of DDX3, and to exclude endogenous human DR5, a murine fibroblast cell line, NIH3T3, was chosen as the host cell for the co-expression of human DR5 and DDX3. 3T3 cells were co-transfected with plasmids encoding His-tagged DDX3 and full-length DR5, DDX3 and a series of deletion mutants of DR5, and DDX3 alone. Cell surface DR5 expression was examined by flow cytometry using TRA-8 staining All transfected cells exhibited similar levels of cell surface DR5, indicating that deletion of the intracellular domain did not alter cell surface DR5. In addition, all transfected cells expressed similar levels of recombinant DDX3, as detected by Western blot analysis of total cell lysates using the anti-6-his antibody. The association of recombinant DDX3 with the deletion mutants of DR5 was examined by co-immunoprecipitation with TRA-8 and Western blot analysis with anti-6-His antibody. The interaction of DR5 with DDX3 is independent of the death domain of DR5. To further define the DR5 binding motif more accurately, further deletion mutants of DR5, D330, and the truncation of DR5 (T300-330), were constructed, co-transfected with DDX3 into 3T3 cells, and analyzed for their interactions. The results demonstrated that DDX3 did not bind to the DR5 death domain but rather to a membrane proximal region (amino acids 300-330) close to the death domain (amino acids 340-420). This indicates that DDX3 might play a different role from previously identified death domain-associated proteins in DR5 signaling. In addition, this region is highly homologous with DR4 and DcR2. These data indicate that DDX3 is a common adaptor protein associated with members of the death receptor family.

DDX3 contains CARD. The functional significance of DDX3 in DR5-mediated apoptosis was next investigated by analyzing the specific property of this molecule. At least two RNA helicases of the DEAD box protein family have been identified recently that contain a caspase recruitment domain (CARD). The CARD in these RNA helicases functions as a regulator for apoptosis. As DDX3 plays an important role in the regulation of DR5-mediated apoptosis, DDX3, a member of the helicases of the DEAD box protein family, can have a CARD as well, and the apoptosis inhibitory function of DDX3 can be directly dependent on the CARD. Thus the possibility that DDX3 is a CARD protein was examined Amino acid alignment analysis indicates that DDX3 contains a conserved action motif between amino acids 50-150, as do MDA5 and RIGI. CARD is a homotypic interaction motif. The proteins containing CARD can interact with each other via this domain. As DDX3 is a novel, highly conserved CARD-containing helicase, it is capable of interacting with other CARD proteins. cIAP1, a CARD-containing protein as well, has been widely regarded as an inhibitor of caspase and is recruited to TNFRI and TNFRII to regulate TNFRI-mediated apoptosis. Whether DDX3 is able to interact with cIAP1 was tested using anti-DDX3 or anti-DR5 antibodies in a co-immunoprecipitation experiment. It was determined that cIAP1 can be readily co-immunoprecipitated with DDX3 and DR5 antibodies in both TRA-8 untreated parental and resistant cells. However, cIAP1 was rapidly released from the DR5-DDX3 complex in TRA-8 sensitive cells, and this was correlated to DDX3 cleavage in the parent cells. In contrast, the cIAP1 levels increased in the DR5-DDX3 complex in resistant cells after TRA-8 treatment. These results indicate that DDX3 could serve as the link between DR5 and cIAP1.

Reverse resistance by knockdown DDX3. To study the role of DDX3 in DR5 signaling, the importance of endogenous DDX3 in TRA-8-induced apoptosis was examined As DDX3 did not decrease in the resistant cells during TRA-8-induced apoptosis, a reduced level of expression of DDX3 can be required for cancer cells to be susceptible to apoptosis. An RNAi strategy was employed to determine the role of DDX3 in the resistance to DR5-mediated apoptosis. An online design tool, BLOCK-IT™ RNAi Designer (Invitrogen), was used to identify RNAi targets for DDX3. Five targeted siRNA sequences were selected from the top 10 highest scoring RNAi targets and cloned into the BLOCK-IT™ U6 entry vector. TRA-8-resistant MDA231 cells were transfected with five RNAi constructs, and protein expression levels of DDX3 were determined by Western blot analysis using monoclonal anti-DDX3 antibody 48 hours post-transfection. Four out of five tested RNAi constructs were very effective (over 50% reduction) inhibitors of DDX3 expression compared to nontransfected or GFP-transfected controls. The most effective of these constructs, #2, was selected for analysis of the effect of DDX3 knockdown in TRA-8-mediated apoptosis. To determine whether knockdown of DDX3 expression reverses TRA-8 susceptibility in TRA-8-resistant cells, TRA-8-resistant MDA231 cells were co-transfected with an RNAi vector (construct #2) and a GFP expression vector as an indicator of transfected cells. 48 hours after transfection, DDX3 was co-immunoprecipitated with DR5. As expected, the expression of DDX3 significantly decreased compared to the control cells. GFP-positive cells were sorted and cultured with various concentrations of TRA-8 overnight. Using the ATPLITE™ assay, MDA231 cells transfected with GFP and control vectors did not undergo apoptosis after TRA-8 treatment, indicating that the cells retained resistance to TRA-8. However, cells co-transfected with the DDX3 RNAi and GFP exhibited TRA-8 dose-dependent cell death. Using TUNEL staining, a significant number of DDX3 knockdown cells were found to be undergoing apoptosis. These results indicate that down-regulation of DDX3 expression reverses TRA-8 resistance. To further determine the causal role of DDX3 in DR5-mediated apoptosis, DDX3 expression was reduced in a panel of tumor cells and their susceptibility to TRA-8-induced apoptosis analyzed. DDX3 RNAi reduced the amount of endogenous DDX3 and enhanced the TRA8-induced apoptosis in the panel of tumor cells, including some spontaneous resistant cells. In contrast, cells transfected with a control oligonucleotide showed normal DDX3 expression and remained resistant to TRA-8-induced apoptosis. Thus, DDX3 is a critical component of the DR5 signal transduction apparatus and is essential for resistance to DR5-mediated apoptosis.

DR5 without DDX3 binding region is pro-apoptotic. To test whether the DDX3 binding motif represents a novel negative regulatory domain modulating the death domain function of DR5, the apoptotic-inducing function of mutant DR5 was compared to the wild-type DR5. Cells transfected with DR5 without death domain appeared to not respond to TRA-8 treatment, but cells transfected with DR5 with a truncated DDX3 binding domain appeared pro-apoptotic and exhibited more susceptibility to TRA-8-induced apoptosis compared to wild-type DR5-transfected cells. There was a pronounced inhibitory effect of DDX3 that could suppress DR5-mediated apoptosis. These findings indicate that DDX3 is an inhibitory mediator of DR5-induced apoptosis.

DDX3 is a CARD protein regulating DR5-mediated apoptosis. To dissect DR5-DDX3-cIAP1 signaling, the region required for its binding to cIAP1 was evaluated. As CARD is at the N terminus of DDX3 and is supposed to interact with cIAP1, this region can be responsible for binding cIAP1. HEK293A cells were transfected with plasmids encoding His-tagged full-length DDX3, DDX3Δ 51-662, DDX3Δ101-662, DDX3Δ151-662, or DDX3Δ1-350. Both full-length and C-terminal deleted DDX3 were able to co-immunoprecipitate cIAP1, the DDX3 with the first 100 amino acids deleted was unable to co-immunoprecipitate cIAP1. These results confirm that the N-terminal CARD of DDX3 is responsible for recruiting cIAP1 to the DR5 complex. It also indicated that the cIAP1 binding motif is located at amino acids 50-100 of DDX3 in front of the cleavage site, amino acids 129-135 (DKSDEDD; SEQ ID NO:30). If DDX3 is cleaved during the DR5-mediated apoptosis, the N-terminal fragment of DDX3 in combination with cIAP1 would be disengaged from the DR5 complex, thereby relieving the inhibition of cIAP1 to death signaling. Thus, DDX3 is a candidate for coupling cIAP1 and death receptors to the apoptosis resistance.

To further substantiate this concept, a dominant negative mutant DDX3 lacking amino acids 1-150 was used. This mutant DDX3ΔCARD (DDX3Δ151-662) fails to interact with cIAP1, but is still able to bind to DR5. Thus, whether DDX3Δ151-662 could be a dominant negative inhibitor of endogenous DDX3 by competing with wild-type DDX3 binding DR5 was assessed. Four types of cells were transfected with DDX3ΔCARD. DDX3ΔCARD-transfected cells exhibited higher levels of expression of DDX3ΔCARD compared to endogenous, full-length DDX3, suggesting that the truncated DDX3 is able to compete with endogenous DDX3 for DR5 binding. cIAP1 was co-immunoprecipitated with the full-length DDX3, but not with DDX3ΔCARD, as analyzed by DR5-co-IP and Western blotting probed with anti-DDX3 and anti-cIAP1 antibody. Furthermore, the susceptibility of transfected cells to TRA-8-mediated apoptosis was examined using the ATPLITE™ assay. Expression of the full-length recombinant DDX3 did not alter the susceptibility to TRA-8-mediated apoptosis as all tested cells remained resistant after TRA-8 treatment. However, TRA-8-resistant tumor cells that expressed high levels of DDX3ΔCARD regained their susceptibility to TRA-8-induced apoptosis after down-regulated DR5 associated cIAP1. These data indicate that the inhibition of cIAP1 to TRA-8-induced-apoptosis is mediated by the intact CARD of DDX3. DDX3 lacking the N-terminal CARD may serve as a dominant negative that partially reverses TRA-8 resistance. The potential susceptibility of cancer cells to TRA-8-induced apoptosis could be regulated by the level of DDX3 and cIAP1 on the DR5 associated complex.

DR5-DDX3-cIAP1 complex inhibits caspase-8 activation. DDX3 was quantified to examine how levels of DDX3 present in the cells correlated with caspase-8 recruitment and processing at the DR5 DISC. MDA231 and UL-3C parental and resistant cells were treated with TRA-8 for four hours, and DR5 was immunoprecipitated with a new anti-DR5 monoclonal antibody (clone: 2B4), which recognizes a different DR5 epitope than TRA-8. The DR5/DDX3/cIAP1 complex was released from the beads, and the DR5-associated DDX3 and cIAP1 were subjected to immunoblotting and sandwich ELISA analysis using anti-DDX3 and anti-cIAP1 antibody. ELISA plates were coated with 2B4 anti-DR5 antibody to capture the immunoprecipitated DR5, and DDX3 and cIAP1 were measured by specific monoclonal antibodies against DDX3 (3E2) and cIAP1. Treatment of either parental-sensitive or induced-resistant tumor cells with TRA-8 did not alter DR5 protein levels. However, the DR5-associated DDX3 levels were significantly altered by TRA-8 treatment in both sensitive and resistant cells. First, untreated resistant cells expressed higher levels of DR5-associated DDX3 compared to untreated sensitive cells as detected by 3E2 anti-DDX3 antibody. Importantly, after TRA-8 treatment, the DR5-associated DDX3 was significantly increased in TRA-8-resistant cells but demonstrated a marked decrease in sensitive cells. The levels of cIAP1 in the DR5 complex were also altered in the same pattern as DDX3. These results suggest that the CARD domain of DDX3 was cleaved and DDX3 was released from the DR5 complex in TRA-8-sensitive cells during apoptosis, whereas DDX3 and cIAP1 were recruited to DR5 upon TRA-8 stimulation in resistant cells rather than sensitive cells.

To form functional DISC, it is essential for cancer cells to release cIAP1 from the DR5 complex to reduce its suppression to caspase during TRA-8-induced apoptosis. This process requires the cleavage of DDX3, indicating that this step is important to initiating a feed-forward apoptosis amplification loop. Because DR5-associated DDX3 resistance to cleavage is correlated with a failure of DISC formation in resistant cells, DDX3 cleavage susceptibility at the DR5-DDX3-cIAP1 complex is different between parental and resistant cells. DR5-associated DDX3 cleavage potential by different caspases was analyzed in both cells. DR5-DDX3-cIAP1 complex was co-immunoprecipitated with anti-DR5 antibody. The eluted fraction from the beads was incubated with active caspase-2 and -8. The cleavage of DDX3 was detected by the Western analysis with anti-DDX3 antibody. These results in combination with ELISA analysis demonstrated that DDX3 cleavage by caspase-8 in resistant cells was highly attenuated compared to sensitive cells, although caspase-2 exhibited similar protease potential in both cells. These results indicate that there is a functional difference in the DDX3 complex between TRA-8-sensitive and -resistant cells. It also indicates that the failure of cleavage of DDX3 by death receptor-associated initial caspases is a key step in the development of TRA-8 resistance.

As cleavage of DDX3 was inhibited in the induced resistant cells, it promoted a study to determine the step in apoptosis signaling in which DDX3 inhibits DR5-mediated apoptosis. The DDX3/cIAP1 complex was predicted to inhibit caspase-8 activation; therefore, the activation of caspase-8 at the DR5-DDX3-cIAP1 complex as one of the first detectable events after receptor triggering was examined. To assess the effect of the DR5-DDX3-cIAP1 complex on caspase-8 activation, the caspase activity was measured using the fluorofenic substrate, Ac-IETD-AMC, incubated with active caspase-8 and DDX3 co-IP eluted fractions from parental sensitive or induced resistant cells. A dose-dependent inhibition of caspase-8 activity was observed over a wide range of dilutions in the DR5 co-IP eluted fraction from resistant cells compared to sensitive cells. In addition, purified cIAP1 also suppressed caspase-8 protease activity completely. It is plausible that DDX3-associated cIAP1 is an inhibitor in the initial activation of caspase-8, thereby preventing the cleavage of DDX3. Thus, these data provided direct evidence that DDX3-cIAP1 can regulate caspase-8 activity and indicates that DDX3-cIAP1 is a specific regulator of caspase-8 engaged by DR5.

The effect of DR5-DDX3-cIAP1 on caspase-8 activation was examined by direct analyses of cIAP1-inhibited caspase-8 in combination with cleavage of DDX3 by caspase assay, and showed that DDX3-cIAP1 also functions as a novel type of caspase inhibitor. The DDX3-cIAP1 complex is capable of arresting death receptor pro-apoptotic signals by suppressing the activation of caspase-8, thereby inhibiting the cleavage of DR5-associated DDX3 by the initial caspase. This model shows that DDX3 protects cells against TRA-8-induced apoptosis via the recruitment of cIAP1 and contributes to the blockage of the death signaling pathways in cancer cells.

Example 2

Figure 2A:
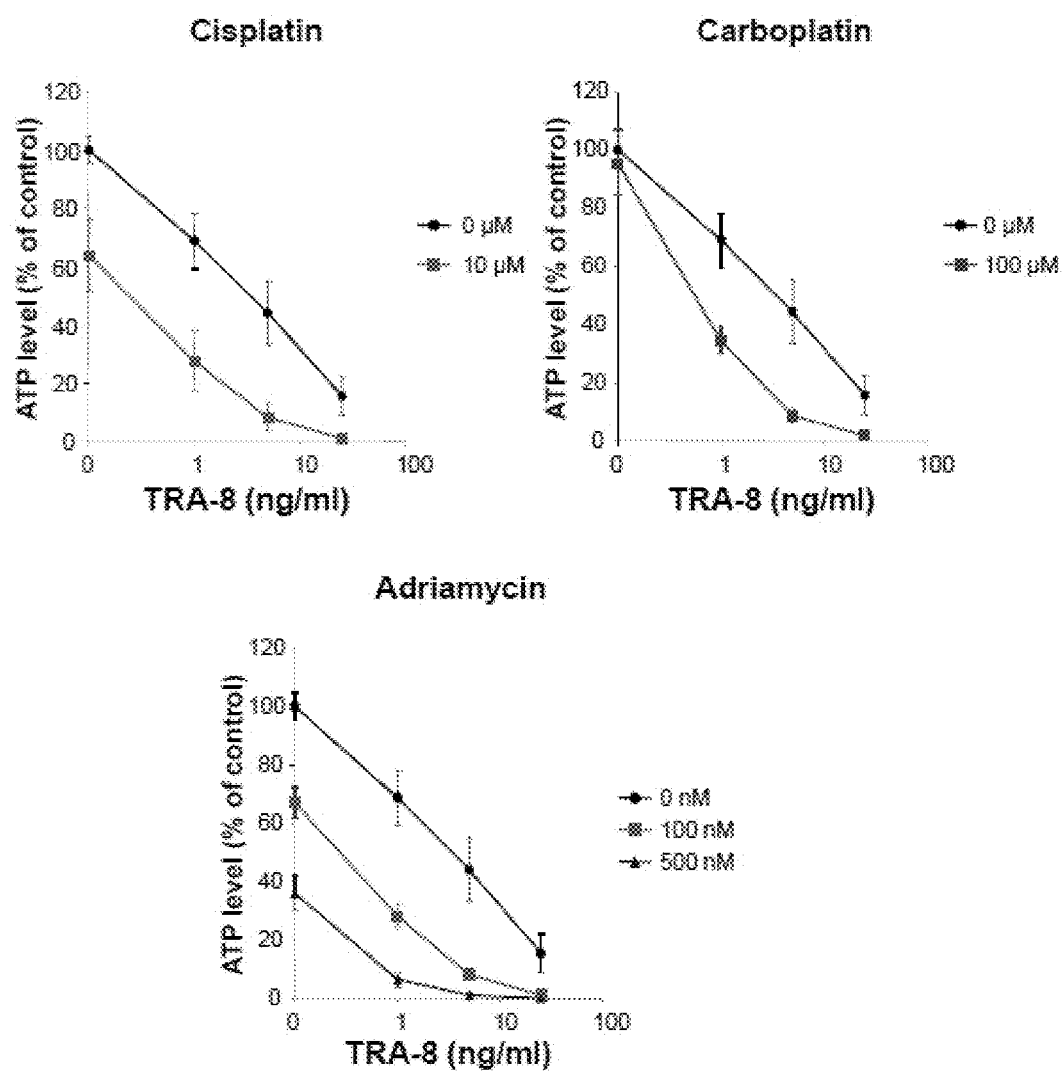
FIGS. 2A and 2B show that combination treatment with TRA-8 and chemotherapeutic drugs leads to additive or synergistic effects on basal A and basal B breast cancer cell lines.
Figure 2B:
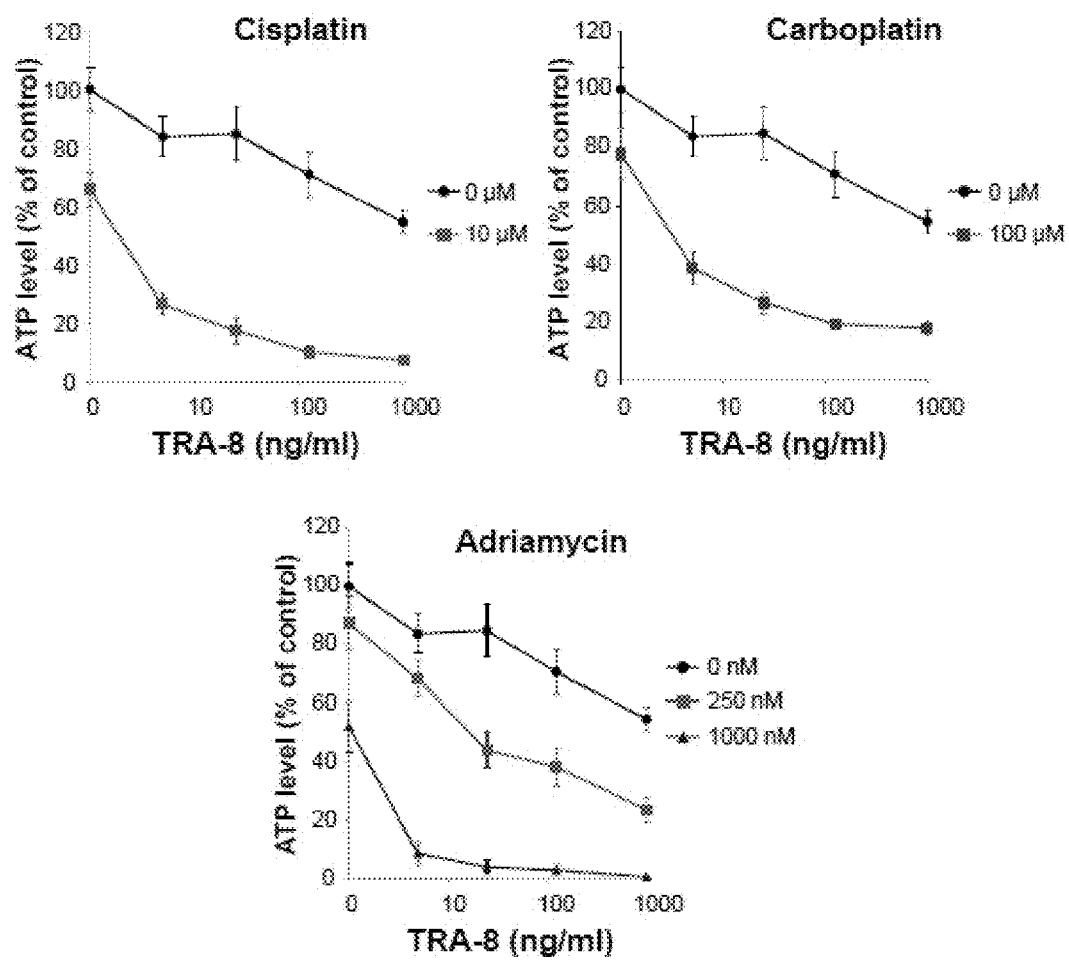

Anti-DR5 Mediated Cytotoxicity to Triple Negative (TN) Basal Breast Cancer Cell Lines A panel of 26 breast cancer cell lines, including 15 cell lines classified as basal (basal A and basal B), 2 HER-2 overexpressing basal, and 9 cell lines that express the luminal phenotype, were used to investigate the relationship between cytotoxic response to TRA-8 (DR5) antibody and breast cancer subtype, as summarized in Tables 3 and 4. TRA-8 induced killing of 12 out of 15 triple negative breast cell (TNBC) cell lines (basal) with $IC_{50}$ values ranging from 0.9 to 4.8 ng/ml (Table 3). The cytotoxicity of TRA-8 against 4 cell lines of basal B subtype is shown in FIG. 1. Equivalent cytotoxicity was produced by TRAIL. Nine luminal breast cancer cell lines were all resistant to TRA-8 (Table 4). Combination treatment with TRA-8 antibody and chemotherapy drugs, including Adriamycin, cisplatin and carboplatin, produced additive to synergistic killing of basal A and basal B breast cancer cell lines (FIG. 2). HCC1937, a BRCA-1 mutant cell line that was resistant to TRA-8, exhibited synergistic cytotoxicity using a combination of TRA-8 and chemotherapy (FIG. 2).

TABLE 3

TRA-8 sensitivity of TNBC cell lines.

| Cell Line | $IC_{50}$ (ng/ml) | Tumor |
|---|---|---|
| SUM149 | 0.9 | Inflammatory ductal carcinoma, 1° |
| 2LMP | 1.1 | Adenocarcinoma, pleural effusion |
| HCC38 | 0.9 | Ductal carcinoma, 1° |
| SUM159 | 1.9 | Anaplastic carcinoma, 1° |
| MDA-MB-436 | 3.2 | Adenocarcinoma, pleural effusion |
| SUM102 | 4.5 | Intraductal carcinoma, 1° |
| BT-20 | 48 | Adenocarcinoma, 1° |
| MDA-MB-468 | 17 | Adenocarcinoma, pleural effusion |
| MDA-MB-152 | 12 | Medullary carcinoma, pleural effusion |
| BT-549 | 18 | Intraductal carcinoma-papillary, 1° |
| HCC1187 | 24 | Ductal carcinoma, 1° |
| MDA-MB-231 | 18 | Adenocarcinoma, pleural effusion |
| HCC1937 | >1,000 | Ductal carcinoma, 1° |
| HCC1143 | >1,000 | Ductal carcinoma, 1° |
| HCC1599 | >1,000 | Ductal carcinoma, 1° |

TABLE 4

TRA-8 sensitivity of $ER^+$ (luminal) cell lines

| Cell Line | $IC_{50}$ (ng/ml) | Tumor |
|---|---|---|
| BT-474 | >1,000 | Invasive ductal carcinoma, 1° |
| DY36T2 (MDA-MB-361 subclone) | >1,000 | Adenocarcinoma, brain metastasis |
| MDA-MB-453 | >1,000 | Adenocarcinoma, pleural effusion |
| MCF-7 | >1,000 | Adenocarcinoma, pleural effusion |
| SK-BR-3 | >1,000 | Adenocarcinoma, pleural effusion |
| ZR-75-1 | 683 | Invasive ductal carcinoma, ascites fluid |
| ZR-75-30 | >1,000 | Invasive ductal carcinoma, ascites fluid |
| T-47D | >1,000 | Invasive ductal carcinoma, pleural effusion |
| MDA-MB-134 | >1,000 | Invasive ductal carcinoma, pleural effusion |

Example 3

Characterization of DR5/DDX3/cIAP1 Apoptosis Inhibitory Complex

Figure 3:
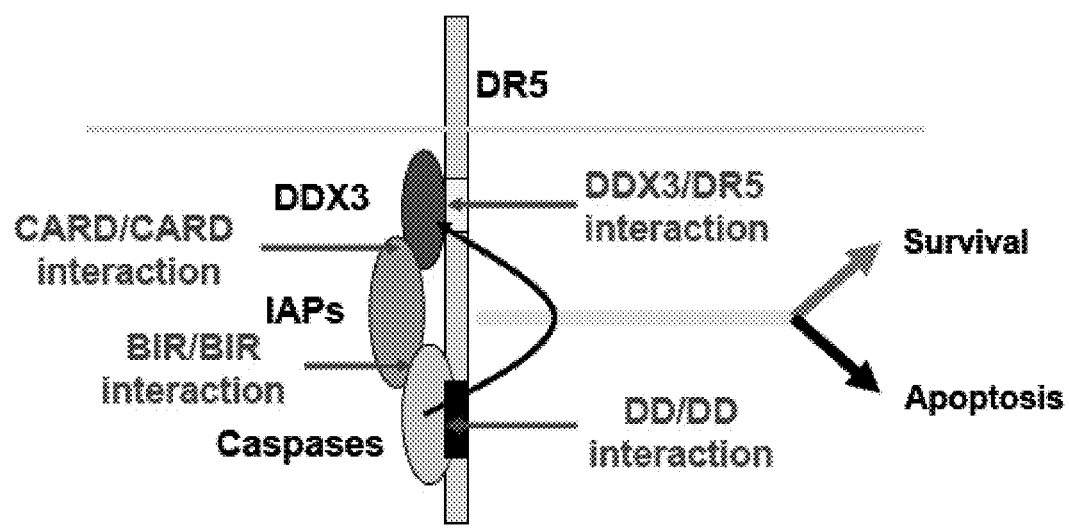
FIG. 3 shows a model of the DR5/DDX3/IAP apoptosis inhibitory complex.

DR5/DDX3/cIAP1 serves as a negative regulation complex which antagonizes the formation and function of DISC as described above. Thus, the DR5-associated DDX3 and recruited apoptosis inhibitors are a predictive biomarker for the susceptibility of cancer cells to DR5-mediated apoptosis. A model is illustrated in FIG. 3. In this model, DDX3 binds to a region proximal of the death domain of DR5. Like other members of the RNA helicase family, DDX3 contains a CARD at its N-terminus, which is responsible for recruiting the Inhibitor of Apoptosis (IAPs) through CARD/CARD interaction. Furthermore, the recruited IAPs inhibit the activity of caspases via its Baculoviral IAP Repeats (BIR) thereby inhibiting initial apoptosis-signal transduction at the death domain. The novelty of this model is the cytoplasmic tail of DR5 contains at least two functionally distinct domains, which interact with each other to determine the apoptosis signal transduction of DR5. When the DDX3/

IAPs complex is dominant over the death domain complex, cancer cells shift toward resistance to DR5-mediated apoptosis. Thus, the DR5-associated DDX3 and cIAP1 may serve as a biomarker for predicting tumor cell's response to anti-DR5 (TRA-8)-mediated apoptosis, and also serve as a drug target for enhancing DR5-mediated apoptosis.

The protein profile of DR5-associated proteins in a panel of cancer cells with defined susceptibility to TRA-8-mediated apoptosis was examined This led to the identification of DDX3 as a novel DR5-associated adaptor protein, which mediates apoptosis resistance at the death domain of DR5.

DR5 lacking DDX3 binding domain is more proapoptotic. As described above, the DDX3 binding domain was mapped to a region of amino acids 300 to 330 of the cytoplasmic tail of DR5. Mutant DR5 with a truncation of this region (D7) lost DDX3 binding while the surface expression of DR5 was not altered. The truncated DR5 exhibited increased spontaneous apoptosis and TRA-8-induced apoptosis compared to cells expressing the wild-type DR5. These results indicate that the cytoplasmic tail of DR5 has a functional region that negatively regulates DR5 apoptosis signal transduction via DDX3 binding.

Figure 4A:
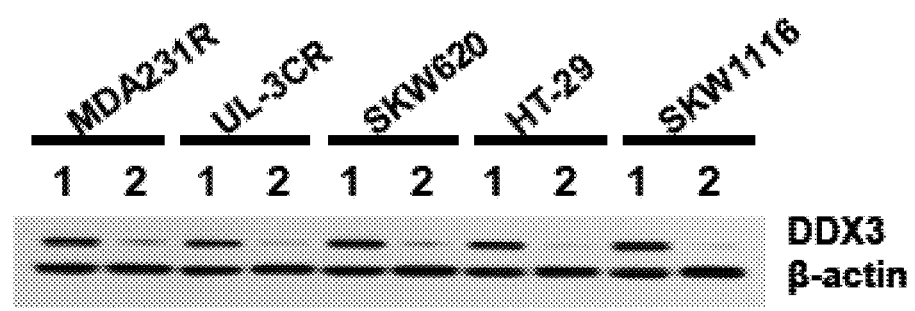
FIG. 4A shows an image of a Western blot demonstrating reduced DDX3 protein expression in cells treated with siRNA directed to DDX3 mRNA.
Figure 4B:
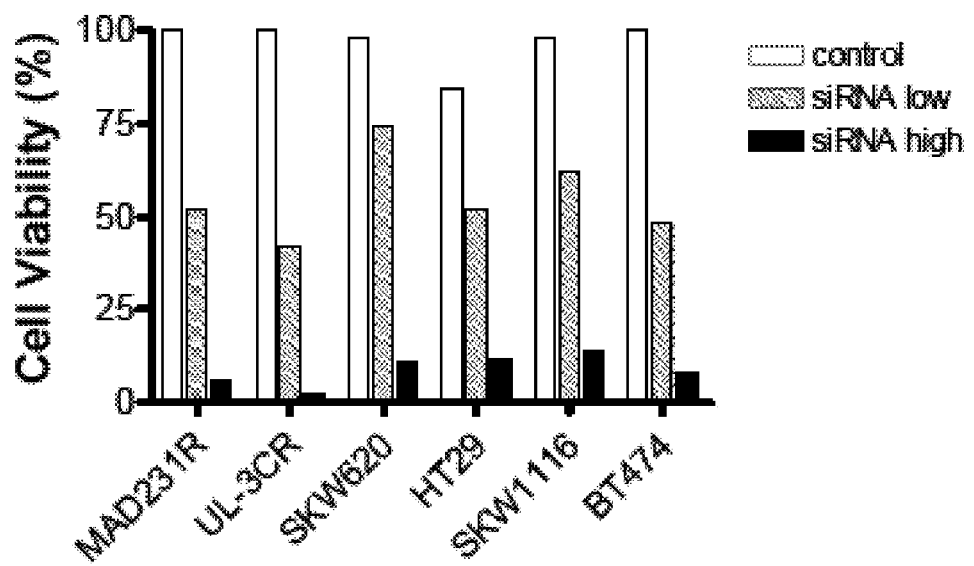
FIG. 4B shows a graph demonstrating increased apoptosis in cells with reduced expression of DDX3 treated with TRA-8 antibody.

Knockdown of DDX3 reverses DR5 apoptosis resistance. Expression of DDX3 in DR5 apoptosis resistant cells including both induced (MDA231R and UL-3CR) and spontaneous resistant cells (SKW620, HT29 and SKW1116) was knocked down with siRNA (FIG. 4A), and the susceptibility of tumor cells to TRA-8-induced apoptosis was analyzed. Apoptosis resistance was reversed in all resistant cells after DDX3 expression was reduced (FIG. 4B), indicating that DDX3 is a negative regulator for DR5-mediated apoptosis.

Figure 5A:
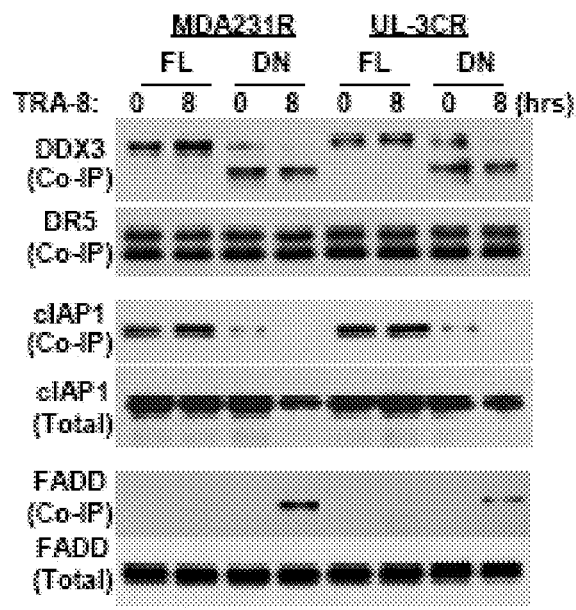
FIG. 5A shows images of Western blots demonstrating that full length DDX3 inhibits apoptosis through the recruitment of cIAP1 to DR5. Cells expressing the CARD-truncated DDX3 (DN) had restored Death Domain Inducing Signal Complex (DISC) function upon treatment with TRA-8 as shown by FADD recruitment.
Figure 5B:
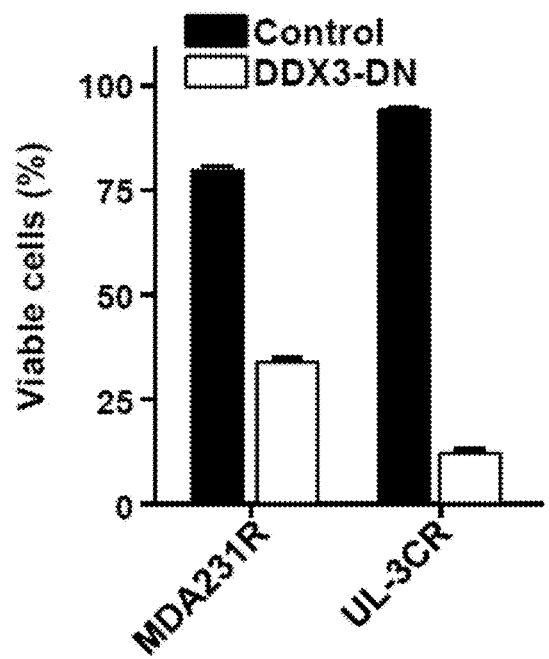
FIG. 5B shows a graph demonstrating that the DR5 resistant tumor cells expressing DDX3 lacking the CARD become more susceptible to TRA-8 induced apoptosis.

DDX3 is a CARD protein that recruits cIAP1 and inhibits DR5-mediated apoptosis. Similar to other helicase proteins such as MDA5 and RIG-1, DDX3 has a conserved CARD at its N-terminus Co-immunoprecipitation showed that the wild-type DDX3 was able to pull-down cIAP1 (FIG. 5A). However, a truncation of the first 100 residues of DDX3 (DN) led to loss of co-immunoprecipitation of cIAP1. The DISC function was restored in cells expressing the CARD-truncated DDX3 as shown by FADD recruitment after TRA-8 treatment. The DR5 resistant tumor cells expressing the DDX3 lacking the CARD became more susceptible to TRA-8-induced apoptosis (FIG. 5B). These results indicate that DDX3 functions as an adaptor protein of DR5. While DDX3 binds to DR5, its CARD recruits cIAP1 thereby inhibiting DR5-mediated apoptosis at the death domain.

Figure 6A:
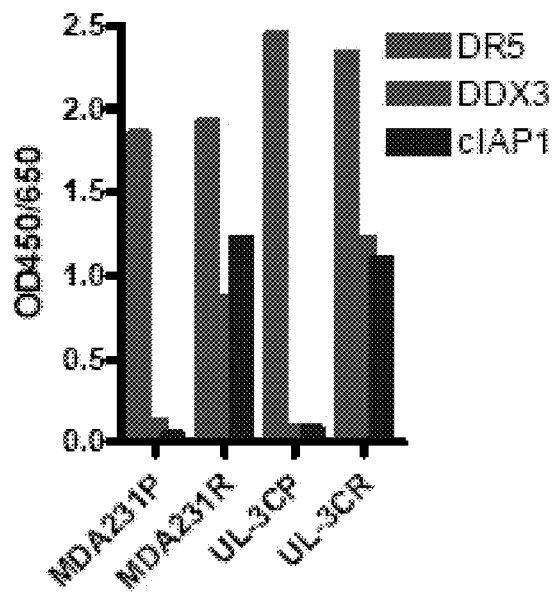
FIG. 6A shows a graph demonstrating that the DR5-associated DDX3 and cIAP1 is lower in the TRA-8 sensitive MDA231P and UL-3CP cell lines than in the TRA-8 resistant MDA231R and UL-3CR cell lines.
Figure 6B:
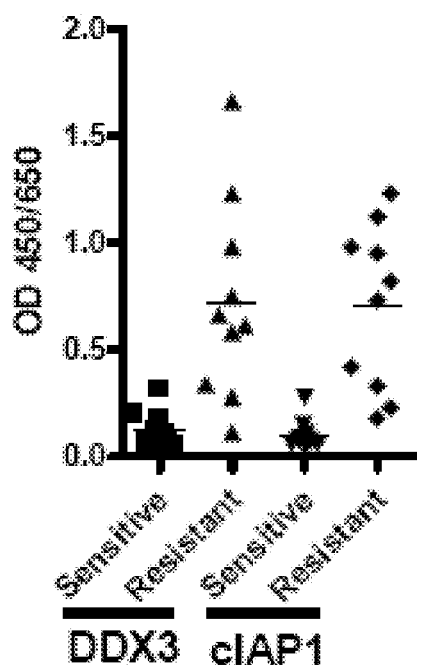
FIG. 6B shows a histogram demonstrating that the TRA-8 resistant cell lines express higher levels of the DR5 associated DDX3 and cIAP1 proteins as compared to a group of TRA-8 sensitive cell lines.

DR5/DDX3/cIAP1 protein complex is a predictive biomarker for DR5-mediated apoptosis. An assay for quantitative measurement of the DR5/DDX3/cIAP1 complex using total cell lysate has been developed. After DR5 co-immunoprecipitation, the amount of DR5, DDX3 and cIAP1 was measured by sandwich ELISA. When DR5 was equally precipitated in both sensitive parental (MDA231P and UL-3CP) and resistant cells (MDA231R and UL-3CR), the associated DDX3 and cIAP1 were lower in the sensitive cells but much higher in the resistant cells (FIG. 6A). A panel of human cancer cell lines with defined TRA-8 susceptibility was further analyzed. A group of TRA-8 resistant cells expressed much higher levels of the DR5-associated DDX3 and cIAP1 compared to a group of TRA-8 sensitive cells (FIG. 6B). These results indicate that the DR5-associated DDX3 and cIAP1 is not only for induction of TRA-8 resistance in induced resistant cells but also in cells that develop spontaneous resistance.

Figure 7A:
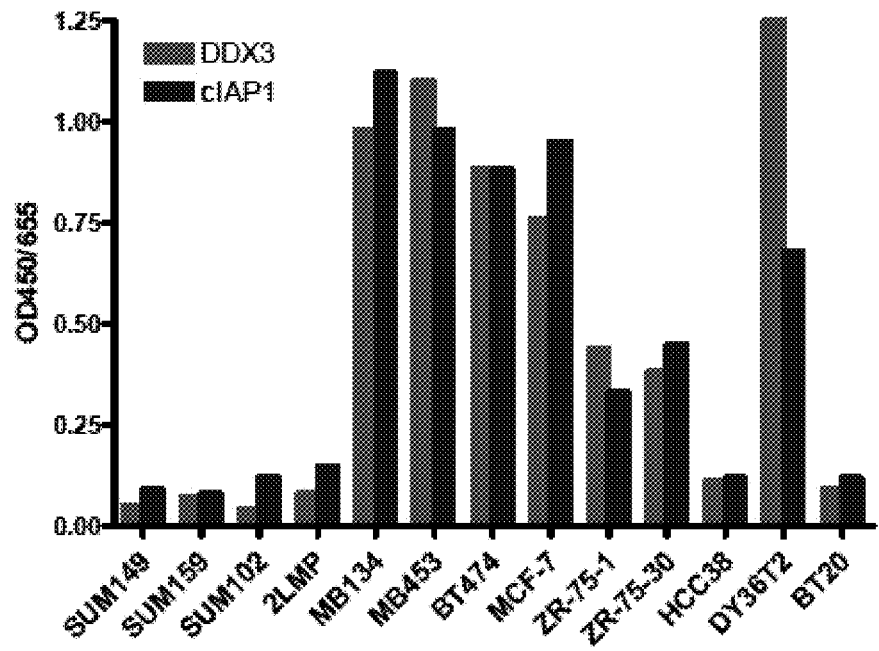
FIG. 7A shows a graph demonstrating the DR5-associated DDX3 and cIAP1 was lower in the triple negative breast cancer cell lines (SUM149, SUM159, SUM102, 2LMP, HCC38, BT20).
Figure 7B:
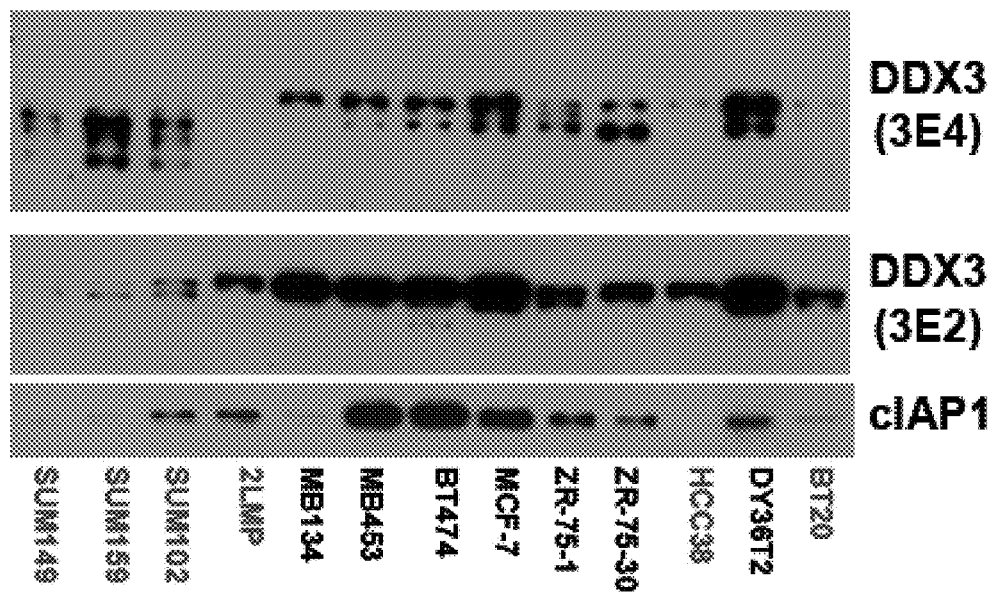
FIG. 7B shows images of Western blots demonstrating that in some triple-negative breast cancer cell lines, the molecular weight of DDX3 that co-immunoprecipitates with DR5 is lower than in non-triple negative breast cancer cells, due to loss of the N-terminal CARD.

DR5/DDX3/cIAP1 protein complex in triple negative breast cancer (TNBC) cells. It has recently been demonstrated that all TNBC cells express cell surface DR5 and are sensitive to TRA-8-induced apoptosis while non-TNBC cells are consistently resistant. Therefore, the DR5/DDX3/cIAP1 complex was examined in a panel of TNBC cell lines. The DR5-associated DDX3 and cIAP1 were lower in TNBC cells (FIG. 7A and Table 5). Interestingly, in some TNBC cells, the molecular weight of DDX3 co-immunoprecipitated with DR5 was smaller as demonstrated by an anti-C-terminal DDX3 antibody, 3E4, (FIG. 7B). This was due to a loss of the N-terminal CARD as determined by the N-terminal CARD specific anti-DDX3 antibody, 3E2. Corresponding to the loss of CARD, the associated cIAP1 was also decreased in these TNBC cells. The proteomic analysis of 2D-SDS-PAGE of DDX3 revealed that DDX3 protein profile was altered in TNBC cells. These results suggest that the DR5/DDX3/cIAP1 complex might be altered in TNBC cells, which may account for the high sensitivity of these cells to TRA-8-induced apoptosis.

Figures 8A, 8B:
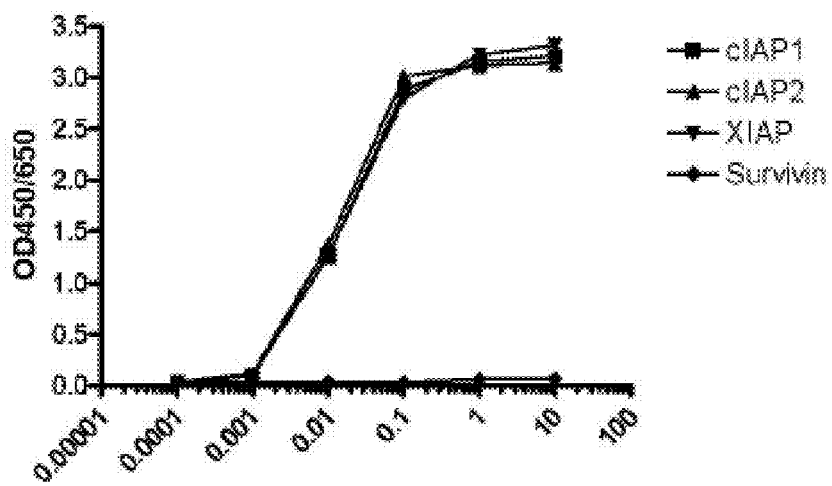
FIG. 8A shows the binding characteristics of 3H4 to cIAP1, cIAP2, XIAP and survivin.
FIG. 8B shows the sequence of the shared epitope recognized by 3H4. Top sequence is second BIR domain for cIAP1 (SEQ ID NO:31); middle sequence is second BIR domain for cIAP2 (SEQ ID NO:32); bottom sequence is second BIR domain for XIAP (SEQ ID NO:33).
Figure 8C:
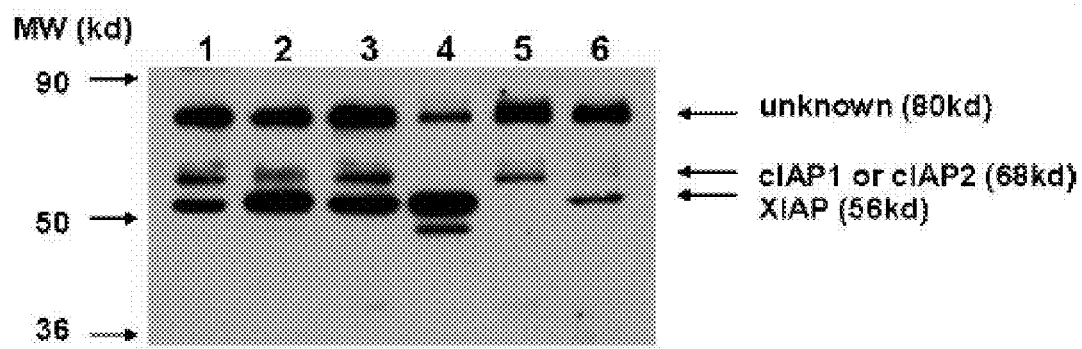
FIG. 8C shows Western blot analysis of total cell lysates from a panel of human pancreatic cancer cell lines with 3H4. Lane 1: MIAcapa; 2: BXPC3; 3: Panc 1; 4: Panc 2.03; 5 S2013; 6: S2VP10.

A novel antibody recognizes BIR. During the screening of the anti-IAP monoclonal antibody pool, a unique monoclonal antibody (3H4) was identified. The 3H4 antibody equally bound to cIAP1, cIAP2 and XIAP but not survivin (FIG. 8A). Because the only common epitope or structure of these proteins is the BIR domain, this particular antibody was suspected to be a BIR domain specific antibody. A series of the truncated IAP proteins was used to map the epitope of the 3H4 antibody, and it was found that the epitope recognized by 3H4 was the second BIR domain of cIAP1, cIAP2 and XIAP (FIG. 8B), which does not exist in survivin. Western blot analysis shown that 3H4 antibody detected 68 kDa cIAP1 or cIAP2 and 58 kDa XIAP. In addition to these known IAP proteins, 3H4 also detected an unknown 80 kDa protein as shown in a panel of pancreatic cancer cell lines (FIG. 8C).

TABLE 5

High sensitivity of TNBC (basal) cells to TRA-8 induced apoptosis correlates with decreased expression of DR5/DDX3/IAP complex.

| Type | Line | IC50 | DR5/DDX3 | DDX3/IAP |
|---|---|---|---|---|
| Luminal | MCF-7 | >1000 | 0.767 | 0.962 |
| | ZR75-1 | 683 | 0.417 | 0.371 |
| | MDA-MB-134 | >1000 | 0.914 | 1.243 |
| HER2, ER+ | DY36T2 | >1000 | 0.645 | 0.967 |
| | ZR75-30 | >1000 | 0.588 | 1.025 |
| HER2, ER− | MDA-MB-453 | >1000 | 1.551 | 1.002 |
| BASAL HER2+, ER− | HCC1569 | 360 | 0.391 | 0.552 |
| | HCC1954 | 488 | 0.522 | 0.960 |
| TNBC (BASAL A) | MDA-MB-468 | 17 | 0.247 | 0.219 |
| | HCC1187 | 24 | 0.629 | 0.356 |
| | BT-20 | 48 | 0.487 | 0.171 |
| | HCC1937 | >1000 | 0.562 | 1.105 |
| | HCC1143 | >1000 | 0.822 | 1.347 |
| TNBC (BASAL B) | SUM149 | 0.9 | 0.018 | 0.026 |
| | HCC38 | 0.9 | 0.367 | 0.048 |
| | 2LMP | 1.1 | 0.178 | 0.218 |
| | SUM159 | 1.9 | 0.038 | 0.134 |
| | SUM102 | 4.5 | 0.133 | 0.155 |
| | BT-549 | 18 | 0.255 | 0.076 |
| | MDA-MB-231 | 18 | 0.212 | 0.158 |

Figure 9A:
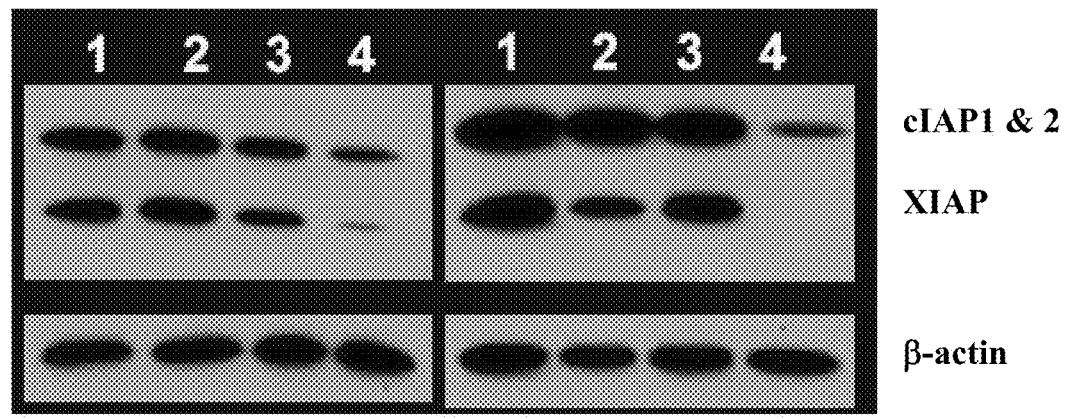
FIG. 9A shows that combination treatment with AT-406 and TRA-8 down-modulates expression of IAP proteins in DR5 apoptosis resistant pancreatic cells. Two human pancreatic cancer cell lines, S2013 (left panel) and S2VP10 (right panel) were treated with control medium (lane 1) or 1000 ng/ml TRA-8 (lane 2), or 10 uM AT406 (lane 3) or both (lane 4) overnight. The IAP proteins in total cell lysates were analysed by western blot with 3H4 antibody.
Figure 9B:
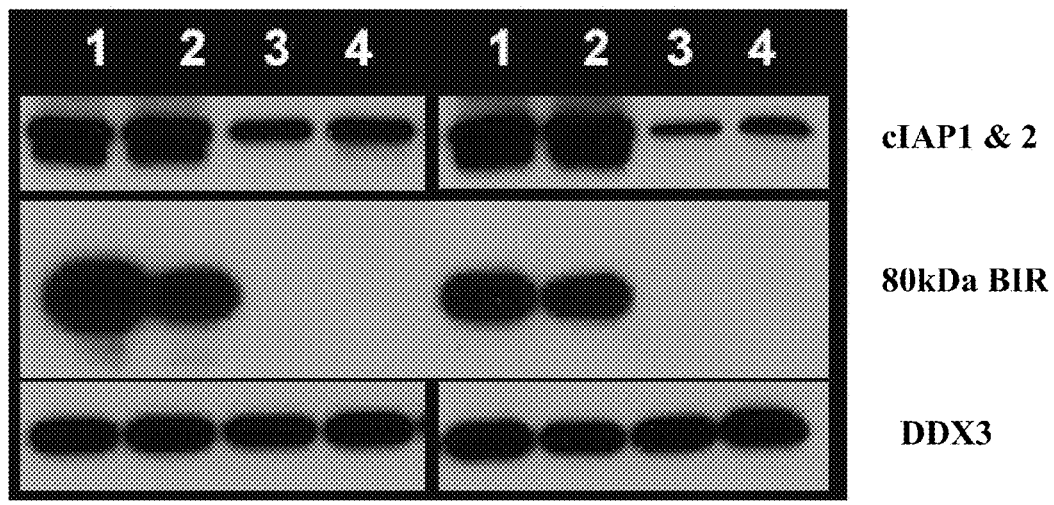
FIG. 9B shows IAP proteins in the DDX3 complex. Cell lysates from above treated cells were immunoprecipitated with an anti-DDX3 antibody (clone 3E4). The precipitated proteins were western blotted and the IAP proteins were detected by 3H4 antibody.

Down modulation of IAPB in the DDX3/IAP complex. N-benzhydryl-5-(2-(methylamino)propanamido)-3-(3-methylbutanoyl)-6-oxodeca-hydropyrrolo[1,2-a][1,5]diazocine-8-carboxamide (AT-406), developed by Ascenta Pharmaceuticals, binds to multiple IAP proteins including cIAP1, cIAP2 and XIAP with low nanomolar affinity. It has been shown that AT-406 synergistically enhances TRAIL-mediated apoptosis. To determine whether AT-406 is able to overcome DR5-apoptosis resistance of pancreatic cancer cells, the effect of AT406 on TRA-8-induced apoptosis was examined for two lines of human pancreatic cancer cells, S2013 and S2VP10, both of which are highly resistant to TRA-8-mediated apoptosis. There were very few apoptotic cells after treatment with 1000 ng/ml of TRA-8. 10 µM AT406 treatment alone did not induce significant cell death. However, the combination treatment resulted in more than 70 % cell death. AT-406 alone did not alter total IAP protein expression as shown by Western blot analysis of total cell lysates (FIG. 9A). However, the combination treatment led to a decrease in all IAPs, demonstrating that synergistic induction of apoptosis promotes AT-406-induced degradation of the IAP proteins. To determine the effect of AT-406 on the DR5/DDX3/cIAP1 protein complex, the amount of cIAP1 was examined by DR5-coIP. There was a dramatic reduction of cIAP1 in the DR5 complex after AT406 alone and combination treatment (FIG. 9B). This was not due to the reduction of DR5-associated DDX3 as DDX3 was equally co-immunoprecipitated with DR5. These results show that AT-406 selectively targets cIAP1 in the DR5/DDX3 protein complex.

Figure 10A:
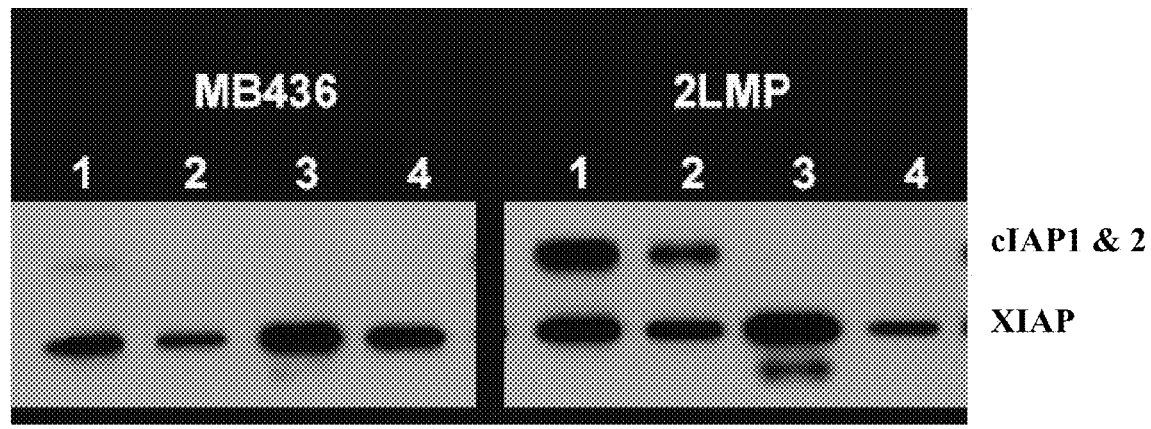
FIG. 10 shows the in vitro effect of AT-406 on IAPs in breast cancer cell lines. Human breast cancer cell lines (MB436 and 2LMP (FIG. 10A), SUM159 and SUM149 (FIG. 10B), BT474 and MB468 (FIG. 10C) were treated with control medium (lane 1) or 1000 ng/ml TRA-8 (lane 2), or 10 uM AT406 (lane 3) or both (lane 4) overnight. Cell lysates from treated cells were immunoprecipitated with an anti-DDX3 antibody (clone 3E4). The precipitated proteins were western blotted and the IAP proteins were detected by 3H4 antibody.
Figure 10B:
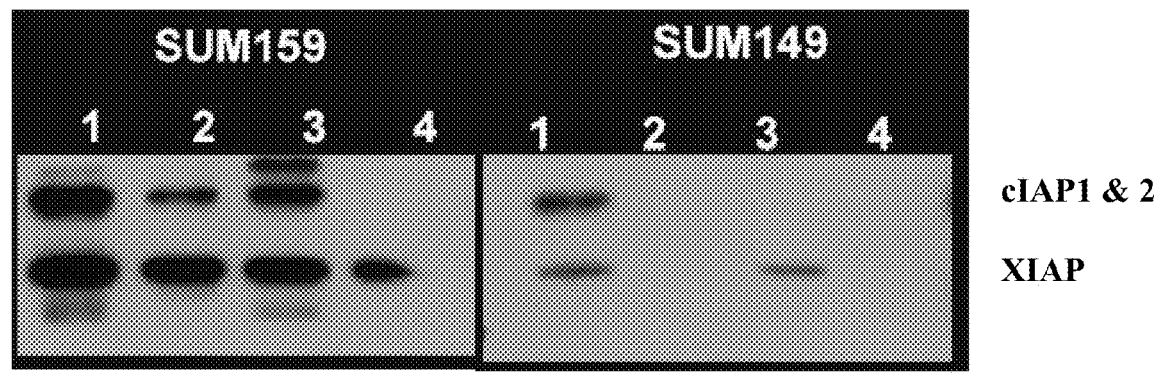
Figure 10C:
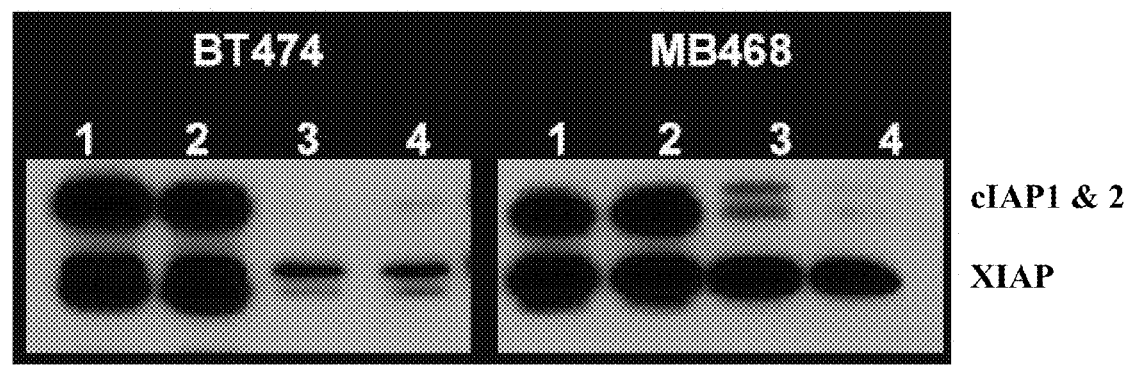

In vitro effect of AT406 on IAPs in breast cancer. Effect of AT406 on expression of IAP proteins in the DDX3 complex was analyzed in a panel of breast cancer cell lines including triple negative and non-triple negative lines. As previously shown, four triple negative breast cancer lines, MB435, 2LMP (FIG. 10A), SUM 159, and SUM 149 (FIG. 10B) expressed lower levels of cIAP1 or cIAP2 protein when co-immunoprecipitated with DDX3, compared to two non-triple negative lines, BT474 and MB468 (FIG. 10C), which were resistant to TRA-8-mediated apoptosis. TRA-8 treatment alone did not change the levels of the IAP proteins. However, AT406 alone (FIGS. 10A-10C, lane 3) or combination with TRA-8 (FIGS. 10A-10C, lane 4) significantly reduced the levels of the IAP proteins associated with DDX3.

Figure 11:
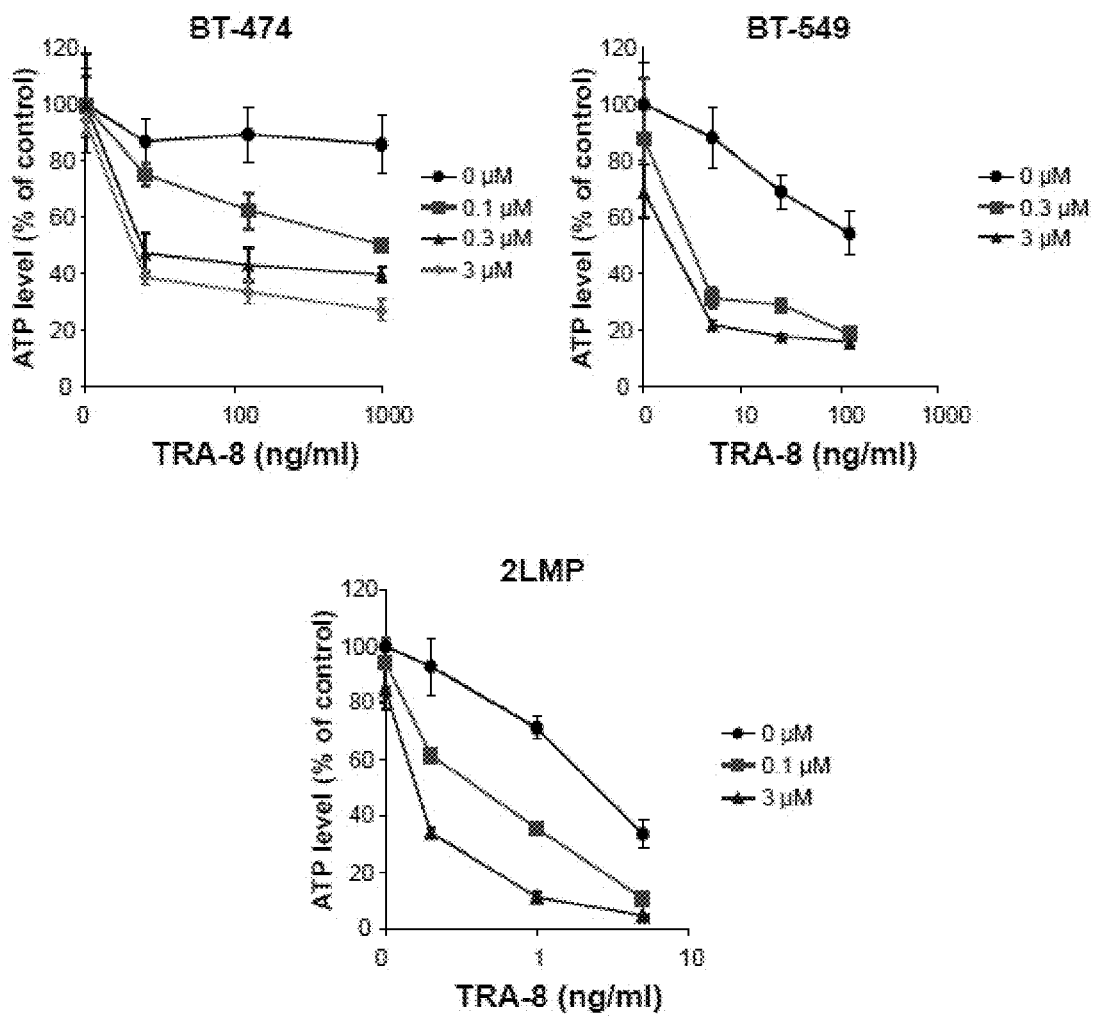
FIG. 11 shows the cytotoxicity produced by combination therapy of TRA-8 and AT406 treatment. Cells were treated with AT-406 for 1 hour followed by 24 hour treatment with TRA-8 and AT-406. Cell viability was determined 24 hours after adding TRA-8 by measurement of ATP levels.
Figure 12:
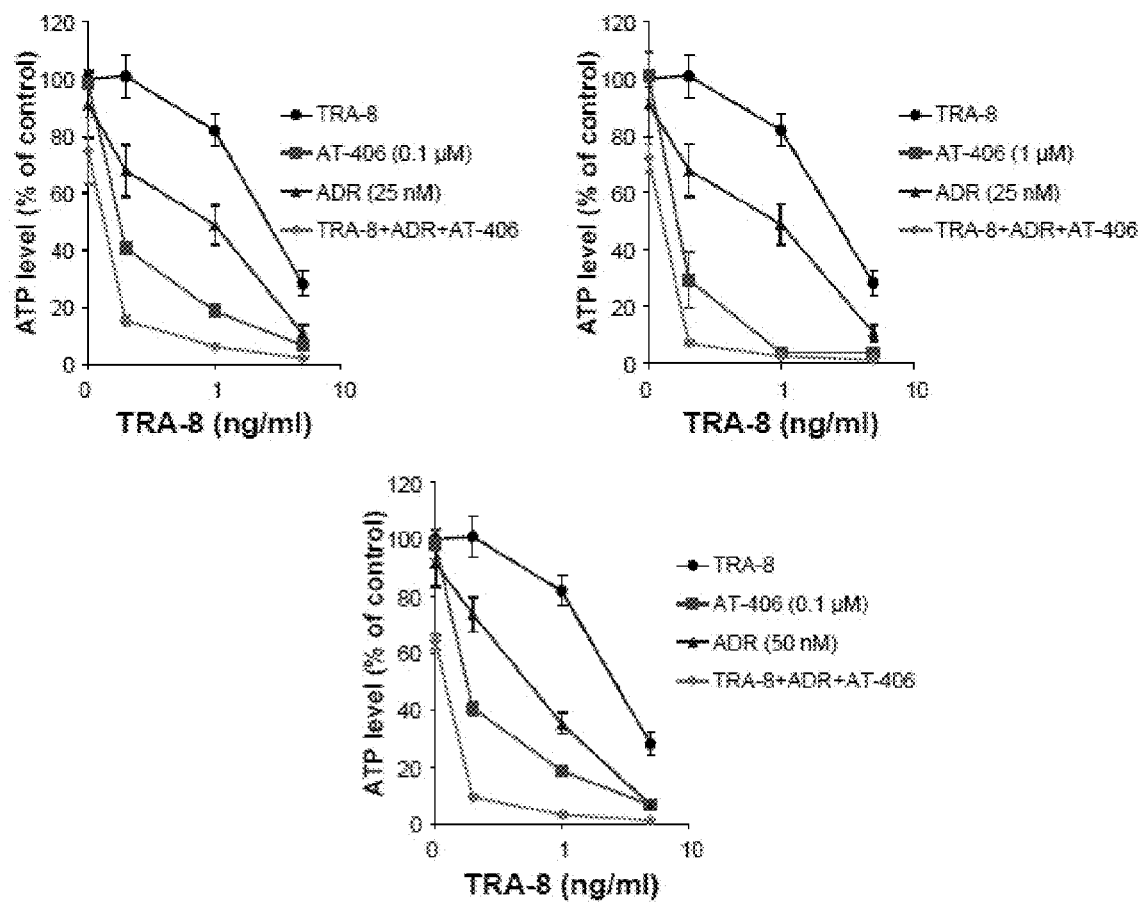
FIG. 12 shows that AT-406 enhances TRA-8 in vitro cytotoxicity in combination with Adriamycin. TRA-8, AT-406, and Adriamycin were used as single agents or in combination. Adriamycin was added 24 hours before AT-406, and TRA-8 was added 1 hour after AT-406. Cell viability was determined 24 hours after adding TRA-8 by measurement of ATP levels.

Cytotoxicity produced by TRA-8 and AT406. The effect of AT-406 on TRA-8 mediated apoptosis against breast cancer cell lines was examined. There was evidence of an interaction between AT-406 and TRA-8 against BT-474, BT-549, and 2LMP cells (FIG. 11). The effect of Adriamycin on AT-406 and TRA-8 mediated apoptosis was also examined. There was enhanced cytotoxicity after combination treatment of 2LMP cells with AT-406, Adriamycin, and TRA-8 (FIG. 12).

Figure 13A:
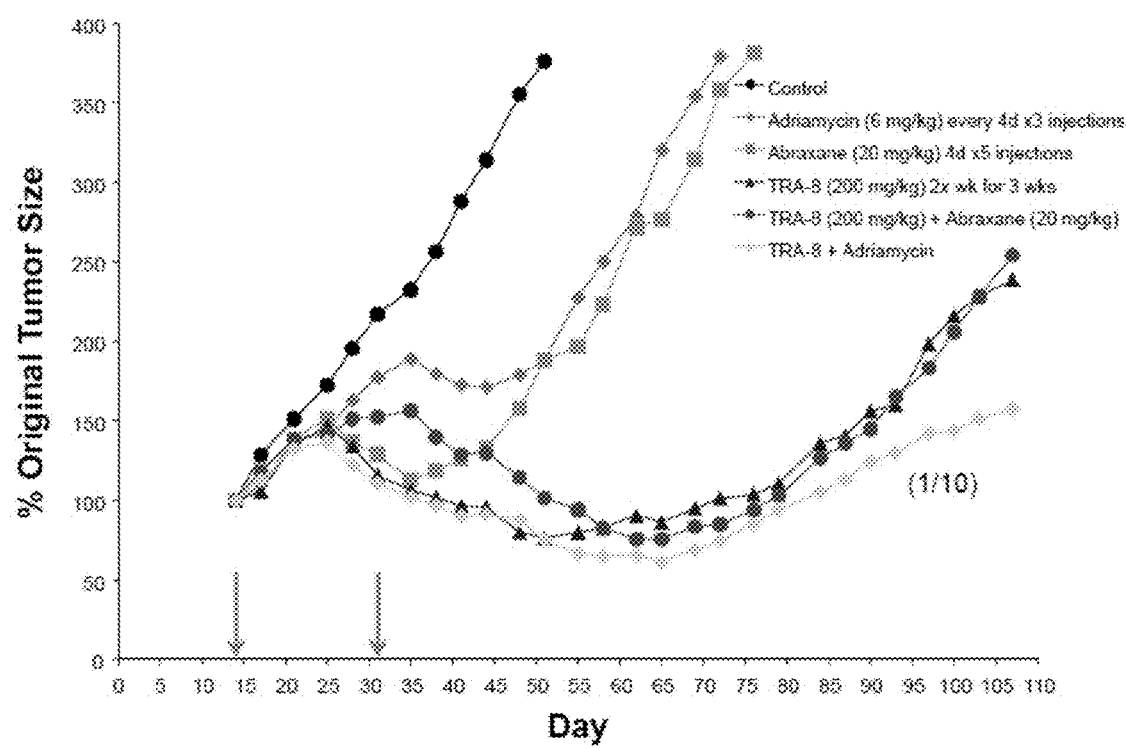
FIG. 13 shows in vivo efficacy of TRA-8 alone or in combination with Abraxane or Adriamycin against orthotopic basal B xenografts in athymic nude mice. SUM159 (FIG. 13A) or 2LMP (FIG. 13B) cells were implanted in the mammary fat pad and treatments began 14 days later when tumors were well established. The arrows indicate the interval during which antibody was administered (n=9-10 mice/group).

In vivo efficacy of TRA-8 and Adriamycin or Abraxane against TNBC xenografts. The in vivo anti-tumor efficacy of TRA-8 alone and in combination with Abraxane or Adriamycin was examined using 2LMP and SUM159 orthotopic basal B xenograft modules in athymic nude mice. Treatments were initiated once tumors were well-established, with tumor diameters of about 6 mm, and tumor size was monitored over time. The mean tumor size of untreated SUM159 tumors doubled in 17.9 days. Treatment of SUM159 tumor bearing mice with TRA-8 alone produced significant inhibition of tumor growth compared to untreated control tumors, with a tumor doubling time of 81.3 days as shown in FIG. 13A, whereas treatment with Adriamycin or Abraxane alone extended the mean tumor doubling time to 41.9 and 49.3 days, respectively. Combination treatment with TRA-8 and Adriamycin resulted in a decrease in mean tumor size that mirrored the tumor growth inhibition by TRA-8 alone and produced a mean tumor doubling time of 84.7 days and 1/10 complete tumor regressions, whereas no complete tumor regressions occurred in mice treated with TRA-8 alone. Animals that were treated with TRA-8 and Abraxane showed similar tumor growth inhibition as those treated with TRA-8 alone or TRA-8 and Adriamycin with a mean tumor doubling time of 74.7 days.

Figure 13B:
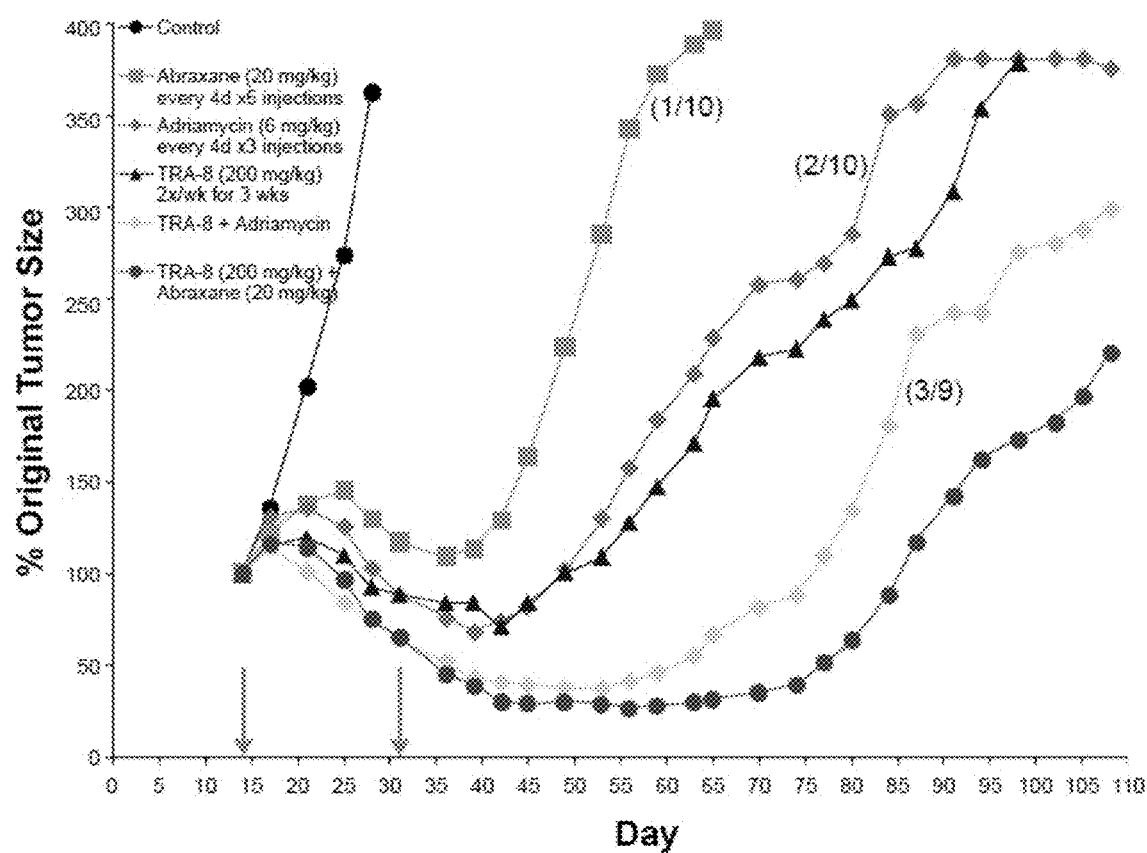

The mean 2LMP tumor size in untreated mice doubled in 8.6 days, as shown in FIG. 13B, demonstrating the rapid growth of this aggressive orthotopic tumor model. Treatment with Abraxane alone produced 1/10 complete tumor regressions and prolonged the tumor doubling time to 46.2 days. Adriamycin was more effective than Abraxane as a single agent against 2LMP xenografts and increased the tumor doubling time to 51.1 days. Treatment with TRA-8 alone significantly inhibited 2LMP tumor growth, extended the tumor doubling time to 58.4 days, and resulted in 2/10 complete tumor regressions. Combination treatment with TRA-8 and Adriamycin resulted in a significant decrease in mean tumor size and increased mean time to tumor doubling to 78.2 days. Combination treatment with TRA-8 and Abraxane was the most effective regimen which increased the mean time to doubling to 87.2 days and produced 2/9 complete tumor regressions. These results demonstrate enhanced in vivo efficacy using chemotherapy drugs in combination with TRA-8 against basal B tumor xenografts.

Figure 14:
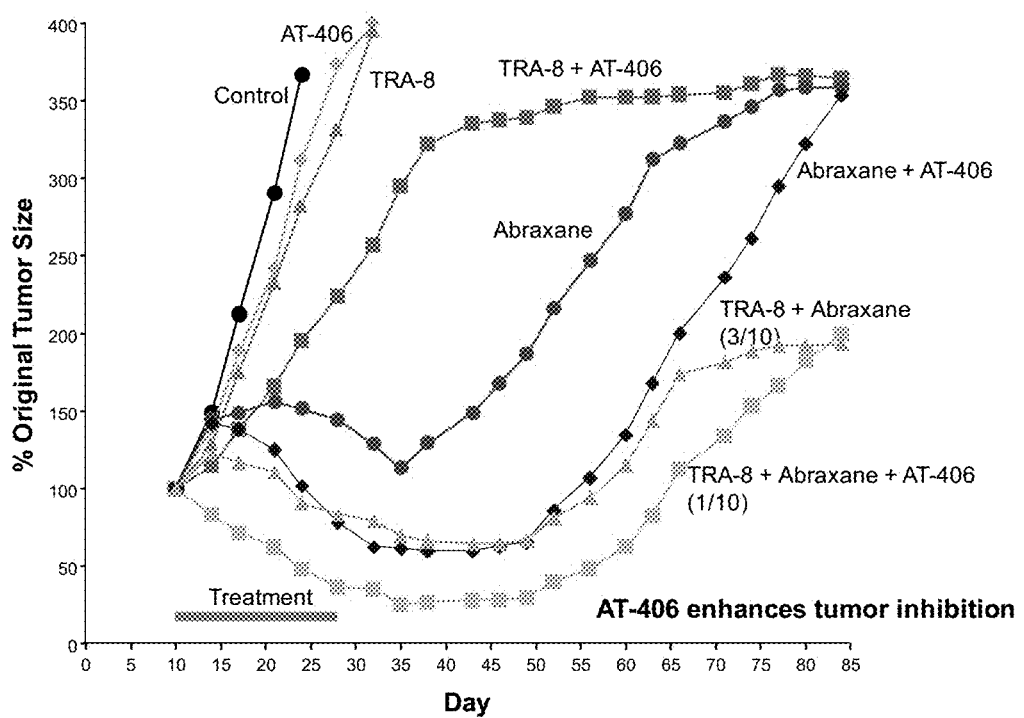
FIG. 14 shows in vivo efficacy of TRA-8 or Abraxane in combination with AT-406 against 2LMP orthotopic basal B xenografts in athymic nude mice. 2LMP cells were implanted in the mammary fat pad and treatments began 10 days later when tumors were well established. The bar indicates the interval during which antibody was administered (n=10 mice/group).

In vivo efficacy of TRA-8, Abraxane, and AT-406. Treatment of 2LMP tumor bearing mice with TRA-8 and AT-406, TRA-8 and Abraxane, or TRA-8 plus Abraxane and AT-406 extended the tumor doubling time compared to treatment with TRA-8, Abraxane, or AT-406 alone (FIG. 14). These results show that the addition of AT-406 enhanced tumor inhibition.

What is claimed is:

1. A method of treating a subject with cancer, the method comprising:
   (a) selecting a subject with a breast cancer, wherein the breast cancer is a basal-like genotype cancer and is HER2 non-amplified, and wherein the breast cancer shows reduced levels of DR5/DDX3/cIAP1 complex as compared to a control; and
   (b) administering to the subject a death receptor agonist, wherein the death receptor agonist is a DR5 agonist.

2. The method of claim 1, wherein the DR5 agonist is an antibody.

3. The method of claim 1, wherein the breast cancer is estrogen receptor negative (ER negative), progesterone receptor negative (PR negative), or both ER negative and PR negative.

4. The method of claim 1, wherein the levels of DR5/DDX3/cIAP1 complex are detected using a whole cell lysate assay.

5. The method of claim 1, wherein the breast cancer comprises a DDX3 lacking a functional N-terminal CARD.

6. The method of claim 5, wherein the DDX3 lacking a functional N-terminal CARD has a truncated or deleted N-terminal CARD.

7. The method of claim 1, wherein the breast cancer is resistant to a chemotherapeutic agent in the absence of the death receptor agonist.

8. The method of claim 7, wherein the breast cancer is resistant to adriamycin.

9. The method of claim 7, wherein the breast cancer is resistant to paclitaxel.

10. The method of claim 7, wherein the breast cancer is resistant to cisplatin or carboplatin.

11. The method of claim 7, further comprising administering to the subject the chemotherapeutic agent.

12. The method of claim 11, wherein the chemotherapeutic agent is administered intravenously every three weeks.

13. The method of claim 1, wherein the death receptor agonist is administered at three week, two week, or one week intervals.

* * * * *

UNITED STATES PATENT AND TRADEMARK OFFICE
CERTIFICATE OF CORRECTION

PATENT NO. : 9,527,915 B2
APPLICATION NO. : 12/940746
DATED : December 27, 2016
INVENTOR(S) : Donald J. Buchsbaum, Tong Zhou and Albert F. LoBuglio Page 1 of 1

It is certified that error appears in the above-identified patent and that said Letters Patent is hereby corrected as shown below:

In the Specification

Column 1, Line 10:
Insert:
-- ACKNOWLEDGEMENTS
This invention was made with government support under grant numbers CA089019 and CA123197 awarded by the National Institutes of Health. The government has certain rights in the invention. --

Signed and Sealed this
Twenty-fourth Day of September, 2019

Andrei Iancu
*Director of the United States Patent and Trademark Office*

SEQUENCE LISTING

```
<160> NUMBER OF SEQ ID NOS: 33

<210> SEQ ID NO 1
<211> LENGTH: 5
<212> TYPE: PRT
<213> ORGANISM: Artificial sequence
<220> FEATURE:
<223> OTHER INFORMATION: Synthetic construct

<400> SEQUENCE: 1

Val Asp Val Ala Asp
1               5

<210> SEQ ID NO 2
<211> LENGTH: 4
<212> TYPE: PRT
```

<213> ORGANISM: Artificial sequence
<220> FEATURE:
<223> OTHER INFORMATION: Synthetic construct

<400> SEQUENCE: 2

Asp Glu Val Asp
1

<210> SEQ ID NO 3
<211> LENGTH: 4
<212> TYPE: PRT
<213> ORGANISM: Artificial sequence
<220> FEATURE:
<223> OTHER INFORMATION: Synthetic construct

<400> SEQUENCE: 3

Ile Glu Thr Asp
1

<210> SEQ ID NO 4
<211> LENGTH: 62
<212> TYPE: DNA
<213> ORGANISM: Artificial sequence
<220> FEATURE:
<223> OTHER INFORMATION: Synthetic construct

<400> SEQUENCE: 4
caccaagctt gcgctatatt cctcctcatt tcgaaaaatg aggaggaata tagcgcctcg    60
ag                                                                   62

<210> SEQ ID NO 5
<211> LENGTH: 62
<212> TYPE: DNA
<213> ORGANISM: Artificial sequence
<220> FEATURE:
<223> OTHER INFORMATION: Synthetic construct

<400> SEQUENCE: 5
aaaactcgag gcgctatatt cctcctcatt tttcgaaatg aggaggaata tagcgcaagc    60
tt                                                                   62

<210> SEQ ID NO 6
<211> LENGTH: 50
<212> TYPE: DNA
<213> ORGANISM: Artificial sequence
<220> FEATURE:
<223> OTHER INFORMATION: Synthetic construct

<400> SEQUENCE: 6
caccggagaa attatcatgg gaaaccgaag tttcccatga taatttctcc                50

<210> SEQ ID NO 7
<211> LENGTH: 50
<212> TYPE: DNA
<213> ORGANISM: Artificial sequence
<220> FEATURE:
<223> OTHER INFORMATION: Synthetic construct

<400> SEQUENCE: 7
aaaaggagaa attatcatgg gaaacttcgg tttcccatga taatttctcc                50

<210> SEQ ID NO 8
<211> LENGTH: 50
<212> TYPE: DNA
<213> ORGANISM: Artificial sequence

```
<220> FEATURE:
<223> OTHER INFORMATION: Synthetic construct

<400> SEQUENCE: 8
caccgccaag tgatattgaa gaataaacgt attcttcaat atcacttggc          50

<210> SEQ ID NO 9
<211> LENGTH: 50
<212> TYPE: DNA
<213> ORGANISM: Artificial sequence
<220> FEATURE:
<223> OTHER INFORMATION: Synthetic construct

<400> SEQUENCE: 9
aaaagccaag tgatattgaa gaatacgttt attcttcaat atcacttggc          50

<210> SEQ ID NO 10
<211> LENGTH: 50
<212> TYPE: DNA
<213> ORGANISM: Artificial sequence
<220> FEATURE:
<223> OTHER INFORMATION: Synthetic construct

<400> SEQUENCE: 10
caccgctttc cagcgggtat attagcgaac taatataccc gctggaaagc          50

<210> SEQ ID NO 11
<211> LENGTH: 50
<212> TYPE: DNA
<213> ORGANISM: Artificial sequence
<220> FEATURE:
<223> OTHER INFORMATION: Synthetic construct

<400> SEQUENCE: 11
aaaagctttc cagcgggtat attagttcgc taatataccc gctggaaagc          50

<210> SEQ ID NO 12
<211> LENGTH: 50
<212> TYPE: DNA
<213> ORGANISM: Artificial sequence
<220> FEATURE:
<223> OTHER INFORMATION: Synthetic construct

<400> SEQUENCE: 12
caccgctgat cggatgttgg atatgcgaac atatccaaca tccgatcagc          50

<210> SEQ ID NO 13
<211> LENGTH: 50
<212> TYPE: DNA
<213> ORGANISM: Artificial sequence
<220> FEATURE:
<223> OTHER INFORMATION: Synthetic construct

<400> SEQUENCE: 13
aaaagctgat cggatgttgg atatgttcgc atatccaaca tccgatcagc          50

<210> SEQ ID NO 14
<211> LENGTH: 21
<212> TYPE: DNA
<213> ORGANISM: Artificial sequence
<220> FEATURE:
<223> OTHER INFORMATION: Synthetic construct

<400> SEQUENCE: 14
ggagaaatta tcatgggaaa c                                         21
```

<210> SEQ ID NO 15
<211> LENGTH: 21
<212> TYPE: RNA
<213> ORGANISM: Artificial sequence
<220> FEATURE:
<223> OTHER INFORMATION: Synthetic construct

<400> SEQUENCE: 15
ggagaaauua ucaugggaaa c					21

<210> SEQ ID NO 16
<211> LENGTH: 21
<212> TYPE: RNA
<213> ORGANISM: Artificial sequence
<220> FEATURE:
<223> OTHER INFORMATION: Synthetic construct

<400> SEQUENCE: 16
guuucccaug auaauuucuc c					21

<210> SEQ ID NO 17
<211> LENGTH: 30
<212> TYPE: DNA
<213> ORGANISM: Artificial sequence
<220> FEATURE:
<223> OTHER INFORMATION: Synthetic construct

<400> SEQUENCE: 17
acggatccaa atgagtcatg tggcagtgga			30

<210> SEQ ID NO 18
<211> LENGTH: 28
<212> TYPE: DNA
<213> ORGANISM: Artificial sequence
<220> FEATURE:
<223> OTHER INFORMATION: Synthetic construct

<400> SEQUENCE: 18
ctctcgagca aagcaggctc agttaccc			28

<210> SEQ ID NO 19
<211> LENGTH: 31
<212> TYPE: DNA
<213> ORGANISM: Artificial sequence
<220> FEATURE:
<223> OTHER INFORMATION: Synthetic construct

<400> SEQUENCE: 19
aaaggtacca gccatggaac aacggggaca g			31

<210> SEQ ID NO 20
<211> LENGTH: 33
<212> TYPE: DNA
<213> ORGANISM: Artificial sequence
<220> FEATURE:
<223> OTHER INFORMATION: Synthetic construct

<400> SEQUENCE: 20
aaagatatct taggacatgg cagagtctgc att			33

<210> SEQ ID NO 21
<211> LENGTH: 34
<212> TYPE: DNA
<213> ORGANISM: Artificial sequence
<220> FEATURE:
<223> OTHER INFORMATION: Synthetic construct -continued

<400> SEQUENCE: 21
acggatccaa atgttttctg gaggcaacac tggg    34

<210> SEQ ID NO 22
<211> LENGTH: 36
<212> TYPE: DNA
<213> ORGANISM: Artificial sequence
<220> FEATURE:
<223> OTHER INFORMATION: Synthetic construct

<400> SEQUENCE: 22
aaagatatct tactgtctca gagtctcagt gggatc    36

<210> SEQ ID NO 23
<211> LENGTH: 36
<212> TYPE: DNA
<213> ORGANISM: Artificial sequence
<220> FEATURE:
<223> OTHER INFORMATION: Synthetic construct

<400> SEQUENCE: 23
aaagatatcc tcgagatttg ctggaaccag cagcct    36

<210> SEQ ID NO 24
<211> LENGTH: 17
<212> TYPE: PRT
<213> ORGANISM: Homo sapiens

<400> SEQUENCE: 24

His Val Ile Asn Phe Asp Leu Pro Ser Asp Ile Glu Glu Tyr Val His
1               5                   10                  15
Arg

<210> SEQ ID NO 25
<211> LENGTH: 13
<212> TYPE: PRT
<213> ORGANISM: Homo sapiens

<400> SEQUENCE: 25

Asp Phe Leu Asp Glu Tyr Ile Phe Leu Ala Val Gly Arg
1               5                   10

<210> SEQ ID NO 26
<211> LENGTH: 10
<212> TYPE: PRT
<213> ORGANISM: Homo sapiens

<400> SEQUENCE: 26

Asp Leu Leu Asp Leu Leu Val Glu Ala Lys
1               5                   10

<210> SEQ ID NO 27
<211> LENGTH: 12
<212> TYPE: PRT
<213> ORGANISM: Homo sapiens

<400> SEQUENCE: 27

Ser Phe Leu Leu Asp Leu Leu Asn Ala Thr Gly Lys
1               5                   10

<210> SEQ ID NO 28
<211> LENGTH: 22
<212> TYPE: PRT

```
<213> ORGANISM: Homo sapiens

<400> SEQUENCE: 28

Thr Ala Ala Phe Leu Leu Pro Ile Leu Ser Gln Ile Tyr Ser Asp Gly
1               5                   10                  15

Pro Gly Glu Ala Leu Arg
            20

<210> SEQ ID NO 29
<211> LENGTH: 11
<212> TYPE: PRT
<213> ORGANISM: Homo sapiens

<400> SEQUENCE: 29

Gln Tyr Pro Ile Ser Leu Val Leu Ala Pro Thr
1               5                   10

<210> SEQ ID NO 30
<211> LENGTH: 7
<212> TYPE: PRT
<213> ORGANISM: Homo sapiens

<400> SEQUENCE: 30

Asp Lys Ser Asp Glu Asp Asp
1               5

<210> SEQ ID NO 31
<211> LENGTH: 49
<212> TYPE: PRT
<213> ORGANISM: Homo sapiens

<400> SEQUENCE: 31

Pro Ser Glu Leu Ala Arg Ala Gly Phe Tyr Tyr Ile Gly Pro Gly Asp
1               5                   10                  15

Arg Val Ala Cys Phe Ala Cys Gly Gly Lys Leu Ser Asn Trp Glu Pro
            20                  25                  30

Lys Asp Asp Ala Met Ser Glu His Arg Arg His Phe Pro Asn Cys Pro
        35                  40                  45

Phe

<210> SEQ ID NO 32
<211> LENGTH: 49
<212> TYPE: PRT
<213> ORGANISM: Homo sapiens

<400> SEQUENCE: 32

Pro Thr Asp Leu Ala Lys Ala Gly Phe Tyr Tyr Ile Gly Pro Gly Asp
1               5                   10                  15

Arg Val Ala Cys Phe Ala Cys Gly Gly Lys Leu Ser Asn Trp Glu Pro
            20                  25                  30

Lys Asp Asn Ala Met Ser Glu His Leu Arg His Phe Pro Lys Cys Pro
        35                  40                  45

Phe

<210> SEQ ID NO 33
<211> LENGTH: 49
<212> TYPE: PRT
<213> ORGANISM: Homo sapiens

<400> SEQUENCE: 33

Pro Arg Glu Leu Ala Ser Ala Gly Leu Tyr Tyr Thr Gly Ile Gly Asp
```

-continued

```
1               5                   10                  15
Gln Val Gln Cys Phe Cys Cys Gly Gly Lys Leu Lys Asn Trp Glu Pro
            20                  25                  30
Cys Asp Arg Ala Trp Ser Glu His Arg Arg His Phe Pro Asn Cys Phe
            35                  40                  45
Phe
```